United States Patent [19]
Clarke et al.

[11] Patent Number: 5,747,297
[45] Date of Patent: May 5, 1998

[54] INDUSTRIAL PHARMACEUTICAL AND COSMETICS APPLICATIONS FOR CULTURED PLANT CELL GUMS

[75] Inventors: Adrienne Elizabeth Clarke, Parkville; Antony Bacic, Eltham; Alan Gordon Lane, Parramatta, all of Australia

[73] Assignees: Bio Polymers Pty. Ltd., Melbourne; Commonwealth Scientific and Industrial Research Organisation, Campbell, both of Australia

[21] Appl. No.: 409,737

[22] Filed: Mar. 23, 1995

Related U.S. Application Data

[63] Continuation-in-part of Ser. No. 920,688, Jul. 28, 1992, abandoned, which is a continuation-in-part of Ser. No. 415,263, filed as PCT/AU88/00052, Feb. 26, 1988, Pat. No. 5,133,979.

[30] Foreign Application Priority Data

Feb. 26, 1987 [AU] Australia .............................. PI0556/87
Sep. 22, 1987 [AU] Australia .............................. PI4502/87

[51] Int. Cl.[6] .................. C12P 19/00; C12N 5/00
[52] U.S. Cl. .................. 435/72; 435/101; 435/410; 435/420
[58] Field of Search .................. 435/240.4, 240.46, 435/101, 72, 420, 410

[56] References Cited

U.S. PATENT DOCUMENTS 4,970,151  11/1990  Yamamoto et al. ............ 435/119

FOREIGN PATENT DOCUMENTS 4053495  2/1992  Japan.

OTHER PUBLICATIONS

Moyna et al. *Planta Med.* 32(3), 1977 pp. 201–205 (see abstract).

Vozumi et al. CA Abstract of (L) above.

Buchala. *Phytochemistry* 13(10) 1974 2185–2188. (abstract).

Baydoun et al. *Planta* 165(2) 1985 pp. 269–276. (abstract).

Carpita et al. Phytochemistry 28(1) 1988, 121–5 (abstract).

Zhao et al. *Acta Pharmacol Sin* 14(3) 1993. pp. 273–276 (abstract).

Sasaki et al. *Plant Cell Physiology* 30(8) 1989. pp. 1159–1170 (abstract).

*Primary Examiner*—Leon B. Lankford, Jr.
*Attorney, Agent, or Firm*—Greenlee, Winner & Sullivan, P.C.

[57] ABSTRACT

Methods of using cultured plant cell gums in the paper, adhesive, oil and gas, ink, lithography, textile, paint, ceramics, cleaning detergent, cosmetics, photography, explosive, firefighting, agricultural, and other industries are described. Industrial and cosmetic compositions containing cultured plant cell gums are also described.

54 Claims, No Drawings

INDUSTRIAL PHARMACEUTICAL AND COSMETICS APPLICATIONS FOR CULTURED PLANT CELL GUMS

RELATEDNESS OF THE INVENTION

The subject application is a continuation-in-part of U.S. Ser. No. 07/920,688, filed Jul. 28, 1992 abandoned which in turn is a continuation-in-part of U.S. Ser. No. 415,263, filed Oct. 25, 1989, now U.S. Pat. No. 5,133,979 the U.S. national phase of PCT/AU88/00052, having an international filing date of Feb. 26, 1988 and a 35 U.S.C. § 371(c) date of Oct. 25, 1989; said PCT/AU88/00052 claiming priority from Australian application PI 0556/87, filed Feb. 26, 1987, and Australian application PI 4502/87, filed Sept. 22, 1987; each of said applications being incorporated herein in the entirety by reference.

FIELD OF THE INVENTION

The subject invention relates to the use of cultured plant cell gums in applications in oil and gas well drilling and production, and in the pharmaceutical, textile, printing ink, lithography, cosmetic, adhesive, paper, paint, ceramic and cleaning detergent industries.

BACKGROUND OF THE INVENTION

A variety of natural and semisynthetic complex carbohydrates or polysaccharides have been commercially important in human and pet food manufacturing; in the cosmetic, paper, textile, paint, agricultural, explosives, hydrolube, adhesive, ceramic, cleaning polish, detergent, fire fighting, ink, photography, lithography, and deodorant gel industries; and in mining, and gas well drilling and production. Natural complex carbohydrates and polysaccharides include seaweed extracts, plant exudates, seed or root extracts, and microbial polysaccharides produced by fermentation. Semisynthetic complex carbohydrates and polysaccharides include cellulose derivatives, low-methoxyl pectin, propylene glycol alginate, triethanolamine alginate and guar gum derivatives. Sandford, P. & Baird, J. (1983) "Industrial Utilization of Polysaccharides" in The Polysaccharides, Vol. 2, pp. 411–491.

The production of natural complex carbohydrates or polysaccharides is frequently problematic. For plant exudates, seed or root extracts, production is dependent on climate and harvest conditions. For example, gum arabic is an exudate from *Acacia senegal* trees. Gum production is stimulated by stripping the bark from the trees; the gum is collected by hand in the form of "dried tears." Production of gum arabic can vary each year as a function of weather conditions, labor strikes, natural disasters, etc. Meer et al. (1975) Food Technology 29:22-30. The unreliable supply results in variable gum arabic cost. Seed gums, such as guar gums are expensive due to harvesting costs. Guar gum is derived from the seed of the guar plant *Cyamopsis tetragonolobus*. Processing involves removal of the seed coat, separation of the germ from the endosperm, and milling of the endosperm. Sandford, P. & Baird, J. (1983), supra.

The production of seaweed extracts can also be problematic. Agar production is labor intensive in that it involves the harvesting of red seaweed by hand: in some areas of the world, divers in full pressure suits collect individual plants in deep water; in other places, the seaweed can be collected at low tide without the use of diving equipment. Carrageenan or Irish Moss is produced from another red seaweed harvested by raking and hand gathering. Algin is produced from brown algae which can be harvested manually or with small mechanical harvesters. Sandford, P. & Baird, J. (1983), supra.

Further, hand harvesting can introduce a purity problem. For example, hand collected lots of gum arabic are seldom pure; samples are classified according to grade which depends on color, and contamination with foreign bodies such as wood or bark (VanNostrand's Scientific Encyclopedia, 7th ed. (1989) D. Considine (ed.), Vol. I, p. 1389).

Microbial fermentation gums such as xanthan gum avoid many of the difficulties associated with harvesting of plant exudates or extraction of algae because production is carried out in fermentation facilities. However, xanthan gum production poses other problems. Xanthan gum is produced by *Xanthamonas campestris*, which presents a cell disposal problem because *X. campestris* is a plant pathogen (Scaad, N. W. (1982) Plant Disease 66(10):882–890). Xanthan gum has also been objected to as being too expensive for certain applications such as drilling mud. See, e.g., Kirk-Othmer Chemical Engineering Encyclopedia (3rd. ed. 1981) 17:153.

Thus, there is a clear need in a number of industries for a reliable, relatively inexpensive gum or class of gums that do not create a disposal problem. While a number of plant cells have been observed to produce polysaccharide and/or complex carbohydrates when cultured (Aspinall, G. & Molloy, J. (1969) Canadian J. Biochem. 47:1063–1070; Fincher, G. et al. (1983) Ann. Rev. Plant Physiol. 34:47–70; Clarke, A. et al. (1979) 18:521–540; McNeil, M. et al. (1984) Ann. Rev. Biochem. 53:625–663; Hale, A. et al. (1987) Plant Cell Reports 6:435–438; and Bacic, A. et al. (1987) Australian J. Plant Physiol. 14:633–641), it has not been suggested that such cultured plant cell gums might be suitable in the pharmaceutical, paper, textile, paint, agricultural, explosives, hydrolube, adhesive, ceramic, cleaning polish, detergent, fire fighting, ink, photography and lithography industries; or in mining, and oil and gas well drilling and production. Only Otsuji, K. et al. EP 0 285 829 (published Oct. 12, 1988) have utilized cultured Polianthes gum in cosmetic applications.

SUMMARY OF THE INVENTION

The subject invention comprises the use of cultured plant cell gums in a variety of industrial, pharmaceutical and cosmetic applications including, without limitation, textiles, paper, adhesives, inks, lithography, ceramics, cleaning detergents, firefighting, agricultural, explosives, oil and gas wells, and cosmetics. Any cultured plant cell gum can be useful in the subject industrial, pharmaceutical and cosmetic applications. Plant cell lines that produce at least about 0.05% (w/v) gum in the final fermenter culture broth, are preferred to reduce production costs. Plant cell lines that produce at least about 0.5%, 2.0%, and 10.0% (w/v) gum in the final culture broth are increasingly preferred. In one embodiment, the cultured plant cell gums employed in such applications are cultured plant cell gums having arabinogalactan proteins (AGPs) of at least about 4.0% (w/w).

In other embodiments, cultured plant cell gums of Phleum, Nicotiana, Pyrus, and Lolium, are employed as viscosifiers, as thickening, gelling, emulsifying, dispersing, suspending, stabilizing, encapsulating, flocculating, film forming, sizing, adhesive, binding and/or coating agents, and/or as lubricants, water retention agents and coagulants. As discussed herein, culture conditions for the plant cells can affect functional properties of the gum product.

Cultured plant cell gum products can be used as a substitute for prior art gums, such as gum arabic and guar gum.

The cultured plant cell gums can also be used as a substitute for xanthan gum, alginic acid, agar, calcium alginate, carrageenan, guar gum, karaya gum, locust bean gum, potassium or sodium alginate, tragacanth gum and others. For example, the cultured plant cell gums can be used as thickening agents and/or emulsifying agents to replace gum arabic in adhesives, inks, textile printing and cosmetics. The cultured plant cell gums can be used to replace alginic acid as an emulsifier, thickening agent, suspending agent, waterproofing agent, etc. in toothpaste, cosmetics, pharmaceuticals, textile sizing, coatings, oil-well drilling muds, and concrete. The cultured plant cell gums can be used to replace agar as a gelling agent, protective colloid, in photographic emulsions or other applications. The cultured plant cell gums can be used to replace calcium alginate as a thickening agent, stabilizer, etc. in synthetic fibers. Carrageenan, which can be used as an emulsifier, protective colloid, stabilizing agent, etc. in toothpastes, cosmetics and pharmaceuticals, can be replaced by cultured plant cell gums. Cultured plant cell gums can substitute for guar gum, which functions as a thickening agent, emulsifier, etc. in paper, cosmetics, pharmaceuticals, textiles, printing, polishing, and as a fracture aid in oil wells. Cultured plant cell gums can also replace karaya gum as a protective colloid, stabilizer, thickener, emulsifier, etc. in pharmaceuticals, textile coatings and adhesives. Cultured plant cell gums can replace locust bean gum (carob-bean gum) as a stabilizer, thickener, emulsifier, etc. in packaging material, cosmetics, sizing and finishes for textiles, pharmaceuticals and paints. Potassium or sodium alginate, which can function as an emulsifier, thickening agent, stabilizer, etc. in pharmaceuticals, textile printing, cement compositions, paper coatings, and in some water-base paints, can be replaced by cultured plant cell gums. Cultured plant cell gums can replace tragacanth gum as an emulsifying agent, coating agent, thickening agent, stabilizer, etc. in pharmaceuticals, adhesives, leather dressings, textile printing and sizing, dyes, toothpastes, hairwave preparations, soap chips and powders. Xanthan gum, which is used as a thickening, suspending, emulsifying agent, stabilizing agent, etc. in oil and gas well drilling muds and other applications, can also be replaced by cultured plant cell gums. In replacing such prior art gums, the cultured plant cell gums can offer unexpectedly improved results. Often, cultured plant cell gums can surprisingly be used in smaller quantities than the prior art gums to achieve equivalent functional results. Further, production of the cultured plant cell gums do not present the cell disposal problem that xanthan gum production does.

The cultured plant cell gums are not useful in applications where their utilities or properties are significantly compromised or destroyed. Organic solvents such as alcohol, acetone and ether and the like can disrupt function by causing precipitation of the cultured plant cell gums. To maintain the gums' emulsification, thickening or gelling properties, it is preferred that the temperature of the gum-containing solution or mixture be maintained between about 40° and 90° C. and have a pH of neutral to slightly alkaline. As the pH increases, the thickening capacity of the gums decreases. However, even at elevated pH, viscosity can increase with increased ionic strength. Gum-containing solutions can gel in the presence of divalent cations such as calcium, and as temperature decreases, gel strength increases. Typically, stable gels are produced in the pH range of between about 3 to 10 and in the presence of calcium ions. Further, heating and cooling of gelled gum solutions between ambient and 80° C. has not reduced gel strength, indicating that the gels can be thermoreversible.

In general, the cultured plant cell gums are useful in a wide variety of applications because they are stable over a wide range of temperatures. In an emulsion or solution, the gums are functional over a temperature range of about 0° to 100° C. at neutral pH. The dried gum powder (neutral pH) is stable over a temperature range of about −70° C. to about 10° C. If heated, the dried, powdered gum can caramelize.

DETAILED DESCRIPTION OF THE INVENTION

The present work is an extension of the work disclosed in U.S. Ser. No. 415,263. That application disclosed the general ability of cultured plant cell gums to function as emulsifying agents, thickeners, stabilizers, texture modifiers, gelling agents, binding or coating agents, and suspending agents. The present work specifically describes and exemplifies non-food industrial, pharmaceutical and cosmetic applications of cultured plant cell gums. "Cultured plant cell gum" is defined as the substantially cell-free material recovered from cultured plant cells, and is used interchangeably herein with "gum product." The cultured plant cells are those which are capable of synthesizing components of the gum product and transporting the same extracellularly in culture. A variety of vascular plant cells, including those derived from gymnosperms and angiosperms, may be used in the subject method. Cells of plants of the Dicotyledonae class (e.g., the Rosidae and Asteridae subclasses) and Monocotyledonae class (e.g., the Commelinidae subclass) can be used in the subject methods. Pyrus, Prunus, Rosa, Nicotiana and Phleum cell lines can produce gums having the preferred concentrations of polysaccharide and/or AGPs. In particular, *Pyrus communis, Prunus avium, Rosa glauca, Nicotiana plumbaginofolia, Nicotiana alata* and *Phleum pratense* cell lines can produce gums that can be useful in the subject methods.

The cultured plant cell gum comprises complex carbohydrates and optionally glycoproteins, which are secreted into the medium by the cultured cells. The major classes of complex carbohydrate polymers are proteoglycans (e.g., arabinogalactan proteins (AGPs)), polysaccharides (e.g., neutral and acidic pectins), hetero-and homo-glucans, heteroxylans, and hetero- and homo-mannans (McNeil et al. (1984) Ann. Rev. Biochem. 53:625–633). Complex carbohydrates and glycoproteins are known to be secreted by many cultured cell lines (Clarke, A. et al. (1979) Phytochemistry 18:521–540; Fincher et al. (1983) Ann. Rev. Plant Physiol. 34:47–70; Bacic, A. et al. (1987) Australian J. Plant Physiol. 14:633–641).

The cells to be cultured can be initiated from, for example, a leaf, style, anther or stem of a plant, segments of which can be placed on solid culture. Callus cells may proliferate from any of the tissues of these organs and the callus cells can then be transferred to liquid suspension culture. Alternatively, seeds can be surface sterilized, and placed in a solid or liquid culture to initiate germination. The germinating seedlings can then be maintained, for a time, in liquid suspension culture. The suspension culture medium can be any known suitable medium such as MS medium (Mirashige, T. & Skoog, F. (1962) Physiologia Plantarum 15:473–497; Wu, M. & Wallner, S. (1983) Plant Physiol. 72:817–820). Transfer to suspension culture is preferred because in general it increases gum production and because it is possible to scale up a liquid suspension culture. Air fermenters are preferred because they reduce shear stress on the cells. While cells can produce gum on a solid medium, mass culture on solid media poses a number of practical difficulties, including gum collection. Usually, a plant cell hormone is employed to enhance cell growth and/or polysaccharide production. Plant hormones include, for example, the auxins such as 2,4-dichlorophenoxyacetic acid (2,4-D) and 2,4-dichlorophenoxybutyric acid (2,4-DB). The specific culture conditions for *N. plumbaginifolia*, *P. communis* and *P. pratense* are exemplified herein.

It has been observed employing BLM as a carbon source increases cell growth and gum yield. It has also been observed that an increase in osmotic pressure or in sucrose concentration in the medium can increase gum production by some cultured plant cells.

The gum product can be recovered from the culture medium by methods well known in the art. See Johns, M. & Noor, E. (1991) Aust. J. Biotechnol. 5(2):73–77; Golueke, C. et al. (1965) U.S. Pat. No. 3,195,271; Seviour, R. & Kristiansen, B. (1983) Eur. J. Appl. Microbiol. Biotechnol. 17:178–181; Mort, A. et al. (1991) Carbohydrate Res. 215:219–237; and Wu, M. & Wallner, S. (1983) Plant Physiol. 72:817–820. A specific recovery and purification method is exemplified herein. A "complexant" is a composition or compound that sequesters calcium or other divalent metal ions from the gum product during the recovery procedure. For example, $Na_2$. EDTA added during the recovery process chelates calcium. Other sequestering agents such as citrate, cyclohexane diamine tetraacetate (CDTA), imidazole, sodium hexametaphosphate may also be used. Sequestering of calcium is desirable to avoid the formation of insoluble complexes during drying of the recovered gum.

The skilled practitioner, using information available in the art and the teachings of the subject application, can identify cultured plant cell gums that are useful as thickening, gelling, emulsifying, dispersing, suspending, stabilizing, encapsulating, flocculating, film forming, sizing, adhesive, binding and coating agents, and as lubricants, water retention agents and coagulants, etc. in the aforementioned industries. The suitability of using a cultured plant cell gum for a particular application can be assessed by methods known to those of skill in the art.

The cultured plant cell gums can be used to establish and stabilize solid, liquid and gaseous dispersions. An emulsion is an intimate mixture of two immiscible liquids in which one phase is dispersed throughout the other as small, discrete droplets (Sandford, P. & Baird, J., "Industrial Utilization of Polysaccharides" in The Polysaccharides (1983), Academic Press, Inc., Vol 2, pp. 411–491). The cultured plant cell gums can be used as emulsifying agents or stabilizing agents in emulsions. Suspensions are solid particles dispersed uniformly throughout a liquid phase (a suspension) mainly by increasing the viscosity of the suspension liquid phase with suspending agent. Foams are gas dispersed in a liquid or solid phase. When cultured plant cell gums are employed as foam stabilizers, they affect the surface properties (e.g., interfacial tension) of foams, thereby promoting a firm, stable foam.

Emulsification capacity can be assessed by, for example, measuring the reduction in aqueous surface tension or interfacial tension due to the gum product, measuring the critical micellar concentration (CMC), or measuring the hydrophile-lipophile balance (HLB; the ratio of polar to nonpolar portions of the composition). Additional methods of assessing emulsifying capacity include particle sizing and counting, and effect on viscosity and electrical properties of the emulsion due to the gum product. For a discussion of such methods, see Zajic, J. & Panchal, C. in CRC Critical Review in Microbiology (1976), pp. 39–66. The choice of a particular gum product for a desired application depends on additional factors such as solubility and compatibility with other chemicals in the emulsion mixture, and pH, ionic strength and temperature of the emulsion mixture. The specific method employed to measure the emulsification capacity for at least some of the gum products described herein involves measurement of turbidity and droplet size and is described in the Examples.

Emulsion stabilizing capacity is the ability of a gum to maintain an emulsion over time. Emulsion stability can be tested by evaluating the turbidity of the emulsion (or industrial emulsion mixture) over time.

Thickening agents increase the viscosity of aqueous solutions or suspensions. They increase the resistance to flow of a liquid. Sandford, P. A. & Baird, J., supra. Viscosity imparted by cultured plant cell gums to mixtures or solutions can be measured with commercially available viscometers. Such viscometers commonly employ methods based on Stoke's law, the capillary tube method, the rotating cylinder method or the oscillating disk method. The specific method employed to measure the viscosity of at least some of the gum products described herein is described in the Examples.

Assessment of gelling capacity of a gum product can be carried out by methods known in the art. The specific method employed to measure gelling capacity of at least some of the gum products described herein is set forth in the Examples. Gelling capacity can be assessed by measuring the rupture strength, shear modulus, back extrusion and melting and setting points of the gum product.

Lubricating capacity can be assessed by methods known in the art. For example, an adaptation of ASTM (American Society for Testing Materials) Method D4172 may be used.

Encapsulating capacity can be assessed by methods known in the art. A specific method is described in Example 3 of the U.S. Patent Application for "Plant Gum Material and Use Thereof in Food Products," filed on even date herewith.

In some cases, particular functional properties have been associated with particular gum components. It has been observed that AGP in the cultured plant cell gum product can enhance emulsification properties. For example, *Pyrus communis* and *Nicotiana Plumbaginifolia* have higher levels (6–11% (w/w)) AGPs, while Phleum pratense produces a gum with nondetectable AGP and poor gelling and emulsification capacity. *Phleum pratense* has comparable viscosity to Pyrus and Nicotiana gums without the gelling and emulsification properties. *Phleum pratense* is thus useful as a viscosity enhancer in applications where emulsification is not desired, e.g., in applications where guar gum and hydroxymethylcellulose have traditionally been used.

Those embodiments of the subject invention which use the gum products as emulsifiers preferably employ a gum product relatively rich in AGPs. In particular, cultured plant cell gums containing at least about 4% (w/w) AGP in the gum can be useful. Complex carbohydrates in the culture fluid can be determined by the method of Dubois et al. (1956) Anal. Chem. 28:350–356. AGP can be determined by the method of Van Holst, G. & Clarke, A. (1985) Anal. Biochem. 148:446–450. AGP-containing gums have been found in higher plants (14 orders of angiosperms, 3 orders of gymnosperms), and in lower plants (e.g., *Fontinalis anti-pyretica*). Fincher, G. et al., supra.

It has been found that a gum product recovered from *Pyrus communis* cells suspension cultured in MS medium plus 2,4-D has complex carbohydrates at about 5.26 mg/ml of culture fluid as determined by the method of Dubois et al. (1956) Anal. Chem. 28:350–356; and 8.9% (w/w) AGP as determined by the method of Van Holst et al. (1985) Anal. Biochem. 148:446–450.

The cultured (MS medium) gum product of *Lolium multiflorum* and *Nicotiana plumbaginifolia* have been found to have an AGP % (w/w) of 11.0 and 4.5, respectively. In contrast, cultured cells (MS medium) of *Phleum pratense* have been found to have no detectable AGP (detection limit is about 0.25 μg by the method of Van Holst et al. (1985)).

A description of particular applications in which the cultured plant cell gums can be employed follows. This discussion is not intended to be limiting.

In the paper industry, prior art gums have been used in wet end beater aids, surface sizes (e.g., size press and calender), pigmented coatings (e.g., blade, roll airknife, and size press coasize press coatings), and in adhesives. Sandford, P. & Baird, J., supra. Cultured plant cell gums can be used as substitutes for such prior art gums as locust bean gum, karaya and guar gums as hydrophilic colloids employed in the wet end as beater aids to reduce flocculation of pulp suspensions and improve paper formation. The cultured plant cell gums can also replace prior art gums as a surface size which is typically applied after the formation of the sheet at calender rolls or at the size press. Sandford, P. & Baird, J., supra. As surface sizes, cultured plant cell gums can impart water resistance, oil and solvent resistance, glue holdout, scuff resistance, physical strength, curl control and gloss. The cultured plant cell gums can also replace such prior art polysaccharides as sodium alginate, which is used as a thickener and dispersant in the pigment coating. The purpose of such an additive is to prevent agglomeration, and to produce adequate flow and leveling of the coating, and to prevent pattern or orange peel in the coating. Sandford, P. & Baird, J., supra.

As exemplified herein, addition of the cultured plant cell gums as a beater aid at the wet end has been observed to result in superior tensile and burst strength, improved resistance to erasure, reduced lint on the paper surface and reduced rate of water penetration as compared paper manufactured without a beater aid. Without wishing to be bound by theory, it is believed that at least some of these improvements are due to a more uniform distribution of pulp fines.

In the adhesives industry, some prior art gums, waxes, tars, and natural resins have functioned as adhesives when dissolved or dispersed in water or organic solvents, applied between substrates and the solution/dispersal allowed to undergo solvent evaporation. Cultured plant cell gums have been found suitable for use in a water re-moistenable adhesive for paper or aluminum foil sheets. The cultured plant cell gum increases viscosity, thereby moderating the flow during application, and the finished film thickness and water retention. The gum product may also serve as a surface attaching agent. The cultured plant cell gum adhesive, when dried on the surface of paper or aluminum sheets, has good affinity for water and does not cause discoloration of the paper or become brittle on aging. The concentration range in the liquid adhesive concentration is between about 1.0 and 3.0% (w/v). The cultured plant cell gums can be used as an adhesive or cement in other applications.

Prior art gums have also been employed in oil and gas field applications including drilling, well completion (cementing and stimulation) and enhanced oil recovery. As used herein, "oil and gas well fluids" refers to all oil and gas well development or production fluids, including without limitation drilling fluids, cementing fluids, and enhanced oil recovery injection fluids. Drilling fluids or muds function to transport drill cuttings to the surface, control formation pressures, maintain bore hole stability, protect productive formations and cool and lubricate the bit and drill string. Prior art gums have been used to impart greater viscosity to the drilling fluid, to act as suspending agents for cuttings and weighting materials, and to reduce loss of water or fluid by preventing penetration into the rock formation. The rheological requirements of the drilling fluid are that it have low viscosity at high shear rates (i.e., at the drill bit), but high pseudoplasticity to suspend solids in laminar flow. When mud circulation stops, the gel strength is preferably sufficient to suspend solids. Sandford, P. & Baird, J., supra; and Kirk-Othmer Chemical Engineering Encyclopedia (3rd. ed. 1981) 17:143–166. These rheology requirements have previously been addressed with combinations of bentonite, cellulose ethers, polyacrylamides and xanthan gum. Drilling mud additives for reduction of fluid loss have included carboxymethylcellulose, polyacrylates and xanthan gum. During well cementing, a cement lining is installed to isolate the productive zone from the remainder of formations. Fluid loss additives are also used during this stage to prevent cement dehydration and minimize water loss to the formation. Sandford, P. & Baird, J., supra. Following drilling and cementing, a completion may be used to remove undesirable formation particles and debris and prevent permeability damage to the producing zone. Completion fluids contain salts for density, and viscosifiers such as xanthan gum to provide suspension for the removal of debris. During well stimulation, hydraulic fracturing and/or acidizing fluids can be used to enhance hydrocarbon productivity. Hydraulic fracturing fluids require suspending agents such as guar or xanthan gums to carry propping solids. Acidizing fluids require a gelling agent effective in high acid concentrations (e.g., 15% HCl). In enhanced oil recovery, the injection fluids contain polymers to increase viscosity, resulting in better oil displacement. Xanthan gum has been a common component in enhanced oil recovery polymer flooding.

It has now been found that cultured plant cell gums can be employed in drilling fluids to increase viscosity, and as emulsifying, suspending, lubricating agents and fluid loss reduction agents. As an emulsifying agent in a drilling mud, the cultured plant cell gums can emulsify and stabilize oil-in-water or water-in-oil mixtures. As a suspending agent, the cultured plant cell gums disperse and suspend cuttings and weighting materials so as to provide a protective colloid for well equipment. As a lubricating agent, cultured plant cell gums can reduce frictional resistance between the drill string and the formation or casing or during string raising and lowering. The strong water affinity of the gum products can prevent water filtration into surrounding strata during drilling or cementing phases. The gum products can also be used as viscosifiers in completion fluids. In hydraulic fracturing fluids, the cultured plant cell gums can be used to impart viscosity, suspend propping solids and as gelling agents. In enhanced oil recovery, cultured plant cell gums can be used to increase viscosity of the injection fluid. The concentration of cultured plant cell gum in the drilling mud, completion, fracturing and enhanced oil recovery injection fluid is between about 0.1 and 3.0% (w/v). For *P. communis* gum, a soft gel begins to form at about 0.5% (w/v).

For each of the foregoing oil drilling applications, the whole fermentation mixture may be used, i.e., without removal of cells. This alternative has the advantage of simplifying the manufacture of oil and gas well fluids. The biodegradability and non-pathogenic nature of the cells makes such alternative possible.

An additional advantage of using cultured plant cell gums in oil and gas field fluids is that they have much less environmental impact than those using palm oil. This is particularly the case for drilling muds prepared for off-shore drilling where it is desirable that leakages from the well be easily dissipated. Aqueous-based drilling muds dissipate more effectively than oil-based muds.

In ink formulations, thickening, suspending and/or emulsifying agents are used to provide the proper viscosity for application and to increase the stability of the ink. Lithographic, letterpress and screen printing inks have higher viscosities and frequently contain thickeners. Flexographic (flexo) and rotogravure (gravure) printing inks have lower viscosities, but use emulsifying or suspending agents for uniform distribution of the pigment and to prevent the ink from separating. Flexographic inks can be alcohol or water based emulsions. Rotogravure inks also contain an emulsion and have the advantages of excellent press stability, printing qualities, the absence of fire hazard and the convenience and economy of water for reduction and cleanup. The ink distribution systems of flexo and gravure printing presses are simple and do not provide the means to distribute and level highly viscous inks; therefore, viscosity is typically 5–100 cP. Letterpress and litho inks can vary in viscosity from under 500 cP for a letterpress-type news ink to over 500 P for special litho ink formulations. In lithography and letter press, uniform and adequate transfer of ink to the printing plate is ensured by a multitude of rollers in the ink distribution unit. Rheology of the litho and letterpress inks is therefore important to roller-to-plate transfer, fidelity in printing, drying speed, holdout, and trapping properties obtained on the substrate. In general, higher press speeds require lower viscosity inks and slower press speeds employ more viscous inks. Low viscosity ink is used in fine-line flexography and shallow-cell gravure printing. Printing smooth, dense solids can best be achieved using higher viscosity ink. Rheology is also important as a color strength determinant. Over-pigmentation leads to a more thixotropic ink, thereby creating a balancing relationship between color intensity and rheology. Kirk-Othmer Chemical Engineering Encyclopedia, supra, Vol. 13, pp.374–376. Lasday, S. (ed.) Handbook for Graphic Communications: (1972) Ink, Paper, Binding, Vol 6., pp. 6–13.

It has been found that cultured plant cell gums can be used as emulsifying, suspending and/or thickening agents in a variety of printing inks, including litho, letterpress, screen printing, flexographic and gravure inks. The gum concentration in flexo inks can be between about 0.5 and 4.0% (w/v).

Additionally, in offset lithography, prior art gums have been used as emulsifying agents and viscosifiers in lithography solutions. Offset lithography is a planographic process where the image and non-image are in the same plane. The image area is oil receptive and the non-image area is water receptive so that following wetting of the plate with the fountain solution, the ink, when rolled across the plate will only be attracted to the oil receptive areas. As used herein, "lithography solution" refers to any non-ink solution used in lithography, including fountain solutions, sensitizing solutions and protecting solutions. The fountain solution is a desensitizing solution which prevents ink from adhering to the plate. Fountain solutions have contained gum arabic, typically at 0.2% (w/w). Lasday, S., supra, Vol. 6, pp. 93–95. The desensitizing use of gum arabic has taken advantage of the good wettability imparted to the fountain solution and also of the viscosity control that allows the wash solution to cling to the plate without running off or forming isolated droplets or pools on the plate. On metal plates, the desensitizing effect might be caused by the formation of an insoluble film of EG Aluminum or Zinc Arabate. A more plausible explanation is that the film of gum is absorbed by the plate. Studies have shown that such films occur on plates of zinc, aluminum, copper, silver, iron tin, lead, glass and fused silica. These films are not mono-molecular but are composed of many molecular layers. LSC Printing Inks, Reinhold Publishing Corporation, New York (1940) pp. 230, 334, 346, 398–9 and 417. Measurement of the wettability of the desensitizing solutions can be evaluated by measurement and study of the contact angles. In this process a section of the plate is partially immersed in water or in a solution of the gum to be tested. The plate is then turned at an angle to the surface of the liquid until the meniscus appears to be eliminated. The resulting angle of the plate to the surface of the liquid is known as the contact angle and is the measure of the wettability of that particular plate with the solution being tested. Read REF Modern Lithography (1951) 47:62.

Cultured plant cell gums can be used as emulsifying agents in sensitizing or fountain solutions for the plates during operation and in protecting solutions during storage. The concentration range of the gum in fountain solutions is between about 0.01 and 2.0% (w/w).

In the textile industry, gums have been used as sizing and thickening agents. Sizing agents act during textile manufacture by binding the loose fibers of the warp, thereby imparting strength, flexibility and smoothness to the warp, allowing weaving to proceed efficiently. Thickeners control the viscosity of various formulations used in the textile industry including dyes, printing inks, coating and flocking solutions. Prior art gums, including guar, algin and xanthan gums have been used in printing and dyeing solutions. Sandford, P. & Baird, J., supra. Cultured plant cell gums can be useful as sizing or thickening agents in the textile industry. As exemplified herein, the gum product can function as a thickening agent for dyestuff used in wool and cotton fabric printing. The concentration range of the gum product in the dyestuff is between about 0.1 and 5.0% (w/v). Modified approaches can be used in the reactive dyestuff process and direct vat dyestuffs for silk and hydrophobic man-made fibers (nylon, acrylics, polyester and acetates).

In the paint industry, viscosifiers, thickeners, emulsifying agents, suspending agents, and dispersants are used to improve flow properties of the paint so that a smooth coat of desired thickness can be applied to a vertical surface without sagging, and to stabilize the paint by preventing coagulation and pigment settling. Thixotropic character of the paint is important in providing good levelling, prevention of running, and avoidance of segregation or stratification of the paint during storage. Sandford, P. & Baird, J., supra; and Gamble, D. & Grady, D., U.S. Pat. No. 2,135,936 (1938). As exemplified herein, cultured plant cell gums can be used as emulsifying agents in an acrylic resin paint or an oil emulsion paint. The concentration range of the gum product in acrylic or oil based paint is between about 0.2 and 0.3% (w/v).

In ceramics manufacturing, a glaze or a colored, opaque or transparent coating is applied to the ceramics before firing. The glaze forms a hard, nonporous surface. Glazes are usually made from powdered glass combined with colored oxides of such elements as cobalt, chrome, manganese or nickel. The mixture of powders is suspended in water and applied to the ceramic surface by spraying brushing or dipping. The glaze is then dried and fixed onto the ceramic surface by firing. Emulsifying agents, suspending agents or dispersants can be used to uniformly distribute the pigments in the glaze. The glaze causes the pigment to adhere to the surface during firing. As exemplified herein, cultured plant cell gums can be used as an emulsifying and suspending agent to produce a glaze of superior consistency, clarity and stability. Further, it has been found that if BLM (Brewers Liquid Maltose) is used as a carbon source during culturing of *N. plumbaginifolia*, the recovered gum product imparts excellent film-forming properties to the glaze. The gum product concentration range in the liquid glaze is between about 0.05 to 3.0% (w/v).

Cultured plant cell gums can also be useful in ceramics forming by plastic extrusion. Completely nonplastic materials can be extruded with the addition of suitable plasticizers such as gums, starches, polyvinylalcohol, waxes and wax emulsions. Grayson, M. (ed.) Kirk-Othmer Concise Encyclopedia of Chemical Technology (1985) p. 237. Cultured plant cell gums can replace prior art gums in such processes. In ceramics forming by slip casting, cultured plant cell gums can be used in the suspension of raw materials to ensure uniform dispersion of the clay and other solid particles in the water.

In cleaning detersive systems, absorption of bath components to the substrate surface may be the most important and fundamental detergency effect. Adsorption is the mechanism whereby the interfacial free energy values between the bath and the solid components (substrate and soil thereon) of the system are lowered, thereby increasing the tendency of the bath to separate the solid components from one another. Surfactant adsorption reduces soil-substrate interactions and facilitates soil removal. Kirk-Othmer Chemical Engineering Encyclopedia, supra, Vol. 22, p. 408. In cleaning detergent manufacturing, the addition of materials to increase viscosity and filmforming properties can enhance surfactant and substrate surface interactions, particularly for vertical surfaces. As exemplified herein, cultured plant cell gums have been found to be useful in improving the viscosity and film-forming properties of detergents. In particular, it has been found that use of BLM as a carbon source in the culturing of *N. plumbaginifolia* produces a gum product that can impart improved film-forming properties to the cleaning detergent. This is particularly useful for cleaning detergents used to clean vertical surfaces. Detergents can also contain soil antiredeposition or suspending agents, such as carboxymethylcellulose, polyvinylalcohol and polyvinylpyrollidone. These antiredeposition agents are believed to function by absorbing onto either the substrate or the soil particle, and imparting electrical charges that reduce the affinity between the soil and substrate. Sandford, P. & Baird, J., supra. It is believed that cultured plant cell gums can also function as an antiredeposition agent by coating the substrate and/or soil particles. The gum product concentration range in cleaning detergents is between about 1 and 10% (w/v).

Cosmetic lotions and creams are water-in-oil or oil-in-water emulsions employing emulsifying and stabilizing agents. Emulsifiers, being surface active agents, lower surface and interfacial tensions and increase the tendency of the lotion or cream to spread. A purified acidic heteropolysaccharides obtained from cultured Polianthes has been used in cosmetic creams, lotions, shampoos and cleansing foams. Otsuji, K. et al. EP 0 285 829, published Oct. 12, 1988. As exemplified herein, cultured plant cell gums can be used without prior purification of gum fractions in cosmetic lotions and creams. The gum product concentration range in the cosmetic lotions and creams is between about 0.5 and 4.0% (w/w).

Other applications for cultured plant cell gums include thickeners, emulsifiers or suspending agents for photographic preparations; thickeners for explosives; thickeners and suspending agents for foundry wash coats; thickeners, foam stabilizers and film formers for fire-fighting fluids; emulsifiers and suspending agents for flowable pesticides, suspension fertilizers and animal liquid feed supplements.

The advantages of the cultured plant cell gums over prior art gums include lower production costs, improved purity and improved production reliability. Because the production of cultured plant cell gums does not rely on labor-intensive harvesting of gum exudate from trees (e.g., as is required for gum arabic) or harvesting of seeds or plants for extraction (e.g., guar gum, agar algin, or carrageenan), and can instead be produced under automated conditions, labor costs associated with the production of cultured plant cell gums can be lower. As discussed hereinabove, in agar production, the harvesting of red seaweed is labor intensive in that it is carried out by hand; in some areas of the world, divers in full pressure suits collect individual plants in deep water; in other places, the seaweed can be collected at low tide without the use of diving equipment. Carrageenan or Irish Moss is produced from another red seaweed harvested by raking and hand gathering. Algin is produced from brown algae which can be harvested manually or with small mechanical harvesters. Sandford, P. & Baird, J. (1983) in The Polysaccharides, Academic Press, Inc. Vol. 2, pp. 411–491. Additionally, since production of cultured plant cell gums is carried out in fermentation facilities, production does not rely on weather and is therefore more reliable than prior art gum production. See, for example, Meer et al. (1975) Food Technology 29:22–30. Further, because cultured plant cell gums are produced in fermentation facilities, they can be purer than prior art gums. As discussed hereinabove, because gum arabic is hand collected, it is seldom pure; samples are classified according to grade which depends on color, contamination with foreign bodies such as wood or bark (VanNostrand's Scientific Encyclopedia, supra at p. 1389).

An advantage of cultured plant cell gums over xanthan gum produced by cultured *Xanthamonas campestris* is that the cultured plant cells do not pose the same cell disposal problem presented by *X. campestris*, a plant pathogen (Scaad, N. W. (1982) Plant Disease 66(10):882–890). Further, cultured plant cell gums are less expensive than xanthan gum for a variety of applications, including drilling fluids (e.g., Kirk-Othmer Chemical Engineering Encyclopedia (3rd. ed. 1981) 17:153).

A further advantage of the subject gum product is that it can often be used in smaller quantities than prior art gums to achieve comparable effectiveness as an emulsifying, stabilization, suspending, thickening, or gelling agent, as a film forming or coating agent, or as a protective colloid.

All references cited are incorporated herein by reference in their entirety.

The following examples are provided for illustrative purposes only and are not intended to limit the scope of the invention.

EXAMPLES

Example 1

Establishing suspension cultures 1.A. —*Phleum pratense*

Seeds var. Kahu from Hodder & Tolley, seed merchants, 17 Binney Rd. Marayong, Australia, were sterilized by rinsing in ethanol and then soaking 5 minutes in hypochlorite ("chlorize" 1:4). The seeds were then rinsed three times with water and transferred to either liquid or solid medium of Hale et al., supra, containing 2 mg/l 2,4-D.

Suspension cultures were initiated from seeds germinating on either liquid culture or callus culture. In the liquid culture, most seeds germinated after five days. The seed and liquid were chopped in a small sterile blender and then returned to an Erlenmeyer flask and shaken for a further two weeks. The resulting culture was propagated by regular subculturing every 2–3 weeks into suspension culture.

The seeds germinating on agar medium began to form callus immediately. The small calli were dissected off and transferred to fresh agar medium. The calli were subcultured every 3–4 weeks. Initially, the calli are mucoid, but after a number of subcultures, they lose their mucoid appearance. Suspension cultures initiated from mucoid calli produced 2–5 g/l of polysaccharide. Suspension cultures initiated from calli that lost their mucoid appearance and no longer produced polysaccharide.

The suspension medium and procedure were those employed in Hale, A. et al., supra.

Within three days of initiation into the suspension medium, culture filtrates are extremely viscous (i.e., filtrate runs from a 5 ml bulb pipette in about 70–80 seconds, as compared to 1.5 seconds for water and 16–20 seconds for Pyrus cell culture filtrate). Also, there is very little growth of cells, so the filtrate volume on harvesting is virtually the same as the culture volume (i.e., the packed cell volume is negligible). While polysaccharide production is lost from callus and suspension cultures on repeated subculture, this does not create a problem as it is easy to initiate a new cell line.

1.B.—*N. plumbaginifolia*

Callus was initiated from seeds cultured on 20–30 ml CSV (Gibson et al. (1976) Planta 128:233–239; and Schenk, R. & Hildebrandt, A. (1972) Can. J. Bot. 50:199–204)) medium (below) solidified with 0.5% (w/w) agar. The callus was maintained on the same solid medium, in the dark at 27°C. Maintenance subculturing occurred approximately every 3 weeks. If drying or discoloration of the culture was observed, it was immediately subcultured.

All stock solutions were made up with Milli-Q™ water in glass bottles.

CS Macro salts

| | |
|---|---|
| $NH_4NO_3$ | 24.8 g |
| $KNO_3$ | 50.1 g |
| $(NH_4)H_2PO_4$ | 9.2 g |
| $CaCl_2.2H_2O$ | 4.0 g |
| $MgSO_4.7H_2O$ | 8.0 g |

The solution was made up to 1 liter with Milli-Q™ water and stored at 1° C. in glass bottles.

CS organics

| | |
|---|---|
| Thiamine-HCl | 100 mg |
| Nicotinic acid | 1000 mg |
| Pyridoxine-HCl | 100 mg |

The solution was made up to 200 ml with Milli-Q™ water and stored at −20° C. in glass bottles.

CS micro salts

| | |
|---|---|
| $MnSO_4.4H_2O$ | 6.5 g |
| $H_3BO_3$ | 2.5 g |
| $ZnSO_4.7H_2O$ | 0.5 g |
| KI | 0.5 g |
| $CuSO_4.5H_2O$ | 100 mg |
| $NaMoO_4.2H_2O$ | 50 mg |

-continued

| | |
|---|---|
| $CoCl_2.6H_2O$ | 50 mg |

The solution was made up to 500 ml with Milli-Q™ water and stored at −20° C. in glass bottles.

CS Iron solution

| | |
|---|---|
| $Na_2EDTA.2H_2O$ | 2.0 g |
| $FeSo_4.7H_2O$ | 1.5 g |

The EDTA was dissolved in 60 ml Milli-Q water, while stirring and heating. It was then cooled to room temperature and the $FeSO_4 \cdot 7H_2O$ was slowly added while also adding NaOH (10M=400 g/liter) to keep pH at 5.9. The solution was made up to 100 ml with water and stored at −20° C. in glass bottles.

To prepare one liter of CSV medium, the stock solutions and solids were mixed in the following quantities in approximately 800 ml of Milli-Q™ water:

| | |
|---|---|
| CS Macro | 50 ml |
| CS Micro | 1 ml |
| CS Iron | 1 ml |
| CS Organics | 1 ml |
| Sucrose | 30 g |
| myo Inositol | 1 g |

The pH was adjusted to 5.8 (20–30 drops of 1M KOH). This medium can be modified in various ways without adverse effect, e.g., inositol can be reduced or deleted. The hormone stocks were added in the following quantities:

2.0 ml 2,4-D (stock 1.0 mg/ml)

0.5 ml of kinetin (stock 0.1 mg/ml).

The solution was then made up to 1 liter with Milli-Q™ water and sterilized for 20 minutes at 10 psi (116° C.).

Suspension cultures were passaged into fresh CSV medium at 7-day intervals using a 10% inoculum (i.e., 2 ml into 20 ml, 20 ml into 200 ml). Suspension cultures were maintained at a 27° C. at a shaker speed of 100 rpm. The cultures were monitored visually for departures from normal color and cell growth patterns. Cultures were also monitored for sterility (i.e., contaminating organisms) and healthy cell morphology (e.g., cell stress).

1.C. —*Pyrus communis* (Green Pear)

Callus was initiated from fruit cultured on 20–30 ml pear BAL (balanced) medium (below) solidified with 0.5% (w/w) agar. The callus was maintained on the same solid medium, in the dark at 27° C. Maintenance subculturing occurred approximately every 4 weeks. If drying or discoloration of the culture was observed, it was immediately subcultured.

All stock solutions for the pear BAL media were made up using Milli-Q™ water in glass bottles. Vitamins and hormone solutions were stored at −20° C.; all other solutions were stored at 1° C.

Macro elements

| | |
|---|---|
| $NH_4NO_3$ | 165 g |
| $KNO_3$ | 190 g |
| $MgSO_4.7H_2O$ | 37 g |

The Macro solution was up to 1 liter with water.

Micro elements

| | |
|---|---|
| $H_3BO_3$ | 1 g |
| $ZnSO4.7H_2O$ | 1 g |
| $MnSO_4.H_2O$ | 1.44 g |
| $NaMoO_4.2H_2O$ | 0.029 g |
| $CuSO_4.5H_2O$ | 0.0025 g(*) |
| $CoCl_2.6H_2O$ | 0.0025 g(*) |

The Micro solution was made up to 100 ml with water. (*) To obtain 2.5 mg of these salts, 25 mg of each was weighed out in separate containers, and dissolved in 10 ml Milli-Q™; 1 ml of each solution was then used.

Vitamins

| | |
|---|---|
| Ca pantothenate | 0.1 g |
| myo-Inositol | 10.0 g |
| Biotin | 0.001 g(*) |
| Nicotinic acid | 0.001 g(*) |
| Thiamine-HCl | 0.1 g |
| Pyridoxine-HCl | 0.05 g |

The vitamin solution was made up to 100 ml with water. (*) A stock solution containing 1 mg of Biotin+1 mg of Nicotinic acid per 10 ml was prepared as follows: 10 mg of both vitamins was dissolved in 100 ml of Milli-Q; 10 ml of this solution was used to make up 100 ml of Stock Vitamins.

$KH_2PO_1$ (potassium dihydrogen orthophosphate)

| | |
|---|---|
| $KH_2PO_4$ | 17 g |

The solution was made up to 1 liter with water.
$CaCl_2.2H_2O$ (calcium chloride dihydrate)

| | |
|---|---|
| $CaCl_2.2H_2O$ | 6 g |

The solution was made up to 100 ml with water.
Fe.EDTA

| | |
|---|---|
| $FeSO_4.7H_2O$ | 6.86 g |
| $Na_2 EDTA.2H_2O$ | 9.17 g |

The EDTA was dissolved in 1 liter of Milli-Q™ (magnetic stirrer, room temperature). The ferrous sulphate was dissolved in the EDTA solution. The resulting solution was brought to a boil, cooled and stored in screw capped glass bottle at 1° C.

KI (potassium iodide)

| | |
|---|---|
| KI | 0.03 g |

The KI was dissolved in 20 ml Milli-Q.
2,4-D (2,4-dichlorophenoxyacetic acid) 0.1 mg/ml

| | |
|---|---|
| 2,4-D | 50 mg |

The 2,4-D was dissolved in 5 ml of commercial grade ethyl alcohol (95%). The 2,4-D was injected slowly under the surface of 495 ml of Milli-Q™ water, using a Pasteur pipette and a magnetic stirrer.

To make up the pear BAL medium, the concentrated stock solutions and solids were mixed (magnetic stirrer) in the quantities indicated below and water added to approximate 900 ml.

| | |
|---|---|
| Macro elements | 10 ml |
| Micro elements | 1 ml |
| Vitamins | 1 ml |
| $KH_2PO_4$ | 10 ml |
| $CaCl_2$ | 2.5 ml |
| Fe.EDTA | 2.5 ml |
| KI | 0.5 ml |
| 2,4-D | 10 ml |
| L-Asparagine | 180 mg |
| L-Ascorbic acid | 50 mg |
| Thiourea | 25 mg |
| Sucrose | 40 grams |

The pH was adjusted to 5.8–6.0 with KOH (0.1 or 1M). The final volume was adjusted to 1 liter with water. For solid medium, 0.5% (5 g/liter) agar was added after adjusting pH and volume. The final medium was sterilized for 20 minutes at 10 psi (116° C.).

Suspension cultures were passaged into fresh BAL medium at 14 day intervals using a 20% inoculum. The cultured were maintained at 27° C. at a shaker speed of 100 rpm. Cultures were monitored for sterility, cell morphology, and departures from normal culture color and cell growth. After subculturing into fresh BAL medium, the packed cell volume (PCV) of the old culture is measured to assess whether the culture conditions are successfully maintaining the cell line in a stable growth pattern. If the PCV declined progressively over several subcultures, the cell line was revived with a single passage on double phosphate pear BAL medium.

1. D—Enhanced polysaccharide production using BLM

When BLM was used as a carbon source to enhance polysaccharide production by Nicotiana or Pyrus, it was typically used at a culture medium concentration of between about 80 to 200 g/liter of medium, or preferably at about 162 g (wet weight) per liter of medium.

Example 2

Recovery of Gum Product from Cultured N. plumbaginifolia

N. plumbaginifolia whole broth was harversted from a fermenter. The whole broth was filtered using a filter having a pore size of about 100 μm. The filtrate was then heated to 80° C. for 30–60 minutes to denature enzymes in the filtrate. The filtrate was then cooled. Complexant (e.g., $Na_2EDTA.2H_2O$; 1 g/l) was added either prior to filtration, after filtration and prior to heating, or after cooling.

In some cases, the filtrate was stored prior to further processing. When storage time was longer than 18 hours, preservatives, 1.0 g/l potassium sorbate and 0.34 g/l sodium metabisulfate, were added. These preservatives allowed storage at ambient temperatures (15°–25° C.) in sealed containers for prolonged periods.

The filtrate, warmed to 30°–800° C. to reduce viscosity, was next concentrated by ultrafiltration (10,000 MW membrane, Amicon Model DC10LA) to about 20–25% of its original volume or until viscosity made further significant concentration difficult. The concentrate was then diafiltered using the same membrane with five equal volumes of distilled $H_2O$, and concentrated again by ultrafiltration to the point at which viscosity or gelling inhibited further progress.

Where the gum product was intended to be used in industrial compositions such as in drilling mud, adhesives, cleaning detergents, dyestuffs, paper, acrylic resin and oil emulsion paints, or printing ink, the concentrate was directly spray dried (Niro Production Minor, Niro Atomizers, Denmark) using a 200° C. inlet temperature and a 100° C. outlet temperature.

Where the gum product was intended to be used in foods, pharmaceuticals, or cosmetics, the concentrate was further purified by an alcohol precipitation method comprising a precipitation and washing step. The concentrate was chilled to 1°–4° C., and NaCl or KCl was added as a concentrated solution, followed by slow addition with stirring of 2–4 volumes cold (1°–4° C.) ethyl or isopropyl alcohol. The NaCl or KCl was added in an amount to give a concentration of 0.03–0.1% w/v in the alcohol-containing mixture. The mixture was allowed to stand at 1°–4° C. for 1–18 hours and then filtered using 2–4 layers of surgical gauze. The filtrate was washed in 67–80% alcohol at 1°–4° C. and the wash was removed by filtration using 2–4 layers of surgical gauze. The alcohol can be recovered and recycled by distillation.

Where further purification was desired, the alcohol purification procedure was repeated one or more times. A variation of the purification procedure comprises repeated precipitation and filtration steps without intervening washing steps.

The purified material was then directly drum dried (Blaw-Knox Co. Buffalo, N.Y.). Alternative drying methods are fluidized bed, vacuum tumble drying and "flash-spin" drying. The purified material can also be spray-dried or freeze-dried if first rehydrated with 1–2 volumes distilled $H_2O$.

Example 3
Functional Assessment of Recovered Gum Products
3.A. —Emulsion Testing: Measurement of Droplet Size, Turbidity and Stability A comparison of the emulsifying properties of Pyrus gum and a prior art gum, gum arabic, was conducted to determine whether the claimed gum has emulsifying qualities comparable or improved relative to the prior art gum. Aqueous solutions of Pyrus gum and gum arabic were mixed with D-limonene oil to produce emulsions, which were then tested for droplet size, turbidity and shelf life stability.

In order to clarify or reduce complexing of the pectic fraction of the Pyrus gum prior to use, 5 grams of Pyrus gum were dissolved in 500 ml of distilled water and boiled for 5 minutes. Concentrated EDTA solution was added until the insoluble pectic material was dissolved. The solution was filtered through two layers of Whatman glass fiber filter paper GF/F under vacuum and dialyzed (MW cutoff 14,000–16,000) against distilled water at 4° C. for 24 hours. The volume of the solution was then reduced under vacuum by rotary evaporation and freeze dried. Gum arabic was obtained from Sigma, No. G-9752. D-Limonene (p-mentha-1,8-diene) was obtained from Bush Boake and Allen.

Stock solutions of gum arabic (250 mg/ml) and Pyrus gum (62.5 mg/ml or 12.5 mg/ml) were pipetted in duplicate to give final concentrations of 0, 0.2, 0.5, 1, 5, 10 and 20% (w/v). The Pyrus solution could not be prepared at concentrations greater than 5% (w/v) due to its viscosity and gelling properties. Twenty percent D-limonene oil in water emulsions were prepared by injecting the oil into the aqueous solutions under the surface of the solutions while being mixed in an Ultraturrax (Ystal T1500, 25–240V, West Germany) at setting 4 for 15 seconds. The speed of the Ultraturrax was increased to setting 7 for 45 seconds to produce the cloud emulsion. The emulsions were allowed to stand for 0.5 hours to allow bubble dispersal.

To determine emulsion capacity, droplet size, turbidity and shelf-life were measured for each emulsion. Emulsion capacity increases with decreased droplet size, increased turbidity and increased shelf-life stability. The droplet size of the cloud emulsion was examined microscopically by placing 2 drops of the emulsion on a slide and diluting with 2 drops of water and estimating droplet size using a calibrated eye piece graticule. Cloud turbidity was measured by diluting duplicate 5 µl aliquots of cloud emulsion into 5 ml of 0.1% (w/v) sodium dodecylsulphate and measuring absorbance at 500 nm. Cloud emulsions were tested for shelf-life stability by centrifuging at 2,500 rpm for 10 minutes and observation of the resulting separation of oil and water phases. The results are set forth in Table 1:

TABLE 1

| Droplet size and turbidity measurement | | | | |
|---|---|---|---|---|
| Conc | Droplet | | Turbidity | |
| (% w/v) | | size (µm) | ABS 500 nm | Abs-Avr |
| Gum arabic | | | | |
| 0 | A | Very large | 0.049, 0.023 | 0.022 |
|  | B | Very large | 0.013, 0.003 |  |
| 0.2 | A | Very large | 0.006, 0.009 | 0.023 |
|  | B | 10–20 | 0.058, 0.022 |  |
| 0.5 | A | 10–20 | 0.042, 0.040 | 0.038 |
|  | B | 4–20 | 0.034, 0.037 |  |
| 1 | A | 6–20 | 0.145, 0.130 | 0.128 |
|  | B | 3–12 | 0.125, 0.112 |  |
| 5 | A | 1–8 | 0.429, 0.366 | 0.336 |
|  | B | 1–6 | 0.273, 0.277 |  |
| 10 | A | 1–10 | 0.482, 0.508 | 0.438 |
|  | B | 1–6 | 0.380, 0.384 |  |
| 20 | A | 0.5–3 | 0.505, 0.522 | 0.464 |
|  | B | 1–4 | 0.404, 0.427 |  |
| Pear | | | | |
| 0 | A | Very large | 0.049, 0.023 | 0.022 |
|  | B | Very large | 0.013, 0.003 |  |
| 0.2 | A | 1–20 | 0.150, 0.136 | 0.127 |
|  | B | 2–20 | 0.115, 0.110 |  |
| 0.5 | A | 1–8 | 0.187, 0.181 | 0.183 |
|  | B | 2–20 | 0.173, 0.194 |  |
| 1 | A | 1–8 | 0.240, 0.223 | 0.252 |
|  | B | 1–6 | 0.275, 0.270 |  |
| 5 | A | 1–2 some larger | 0.577, 0.592 | 0.653 |
|  | B | 1–3 some larger | 0.776, 0.670 |  |

*A and B are duplicates.
The Table 1 results are graphed in FIG. 2.

TABLE 2

| Shelf life stability | | |
|---|---|---|
| Conc | Emulsion Description[1] | |
| (% w/v) | Before | After centrifugation |
| Gum arabic | | |
| 0 | Oil layer | Oil layer |
|  | Water layer | Water layer |
| 0.2 | Oil film | Oil layer |
|  | Cream layer | Water layer |
|  | Water layer |  |
| 0.5 | Oil film | Oil layer |
|  | Cream layer | Water layer |
|  | Water layer |  |
| 1 | Cream layer | Oil layer |
|  | Water layer | Cream layer |
|  |  | Water layer |
| 5 | Cream layer | Cream layer |
|  | Water layer | Water layer |
| 10 | Cream layer | Cream layer |
|  | Water layer | Water layer |
| 20 | Cream layer | Cream layer |
|  | Water layer | Water layer |

TABLE 2-continued

<table>
<tr><th rowspan="2">Conc<br>(% w/v)</th><th colspan="2">Shelf life stability</th></tr>
<tr><th colspan="2">Emulsion Description[1]</th></tr>
<tr><td></td><td>Before</td><td>After centrifugation</td></tr>
<tr><td>Pear</td><td></td><td></td></tr>
<tr><td>0</td><td>Oil layer<br>Water layer</td><td>Oil layer<br>Water layer</td></tr>
<tr><td>0.2</td><td>Oil film<br>Cream layer<br>Water layer</td><td>Oil film<br>Cream layer<br>Water layer</td></tr>
<tr><td>0.5</td><td>Oil film<br>Cream layer<br>Water layer</td><td>Oil film<br>Cream layer<br>Water layer</td></tr>
<tr><td>1</td><td>Cream layer<br>Water layer</td><td>Cream layer<br>Water layer</td></tr>
<tr><td>5</td><td>Cream</td><td>Cream</td></tr>
</table>

[1]Descriptions taken from duplicate emulsions.

From the foregoing results, it is seen that when emulsifying 20% D-limonene in water, Pyrus gum on a weight for weight basis produces smaller droplets at a lower concentration than gum arabic. For example, at 0.2% (w/v) of Pyrus gum, the emulsion mixture has a film of free oil, a cream layer stable to centrifugation, oil droplets of 1–20 μm and a cloud turbidity at 500 nm of 0.127. In contrast, 0.2% (w/v) gum arabic in an emulsion mixture has an unstable cream which separates completely to oil on centrifugation, has a larger droplet size (10–20 μm) and an average cloud turbidity reading of 0.023 at 500 nm. These results indicate that the Pyrus gum has improved emulsifying qualities relative to those of gum arabic at the same concentration.

Emulsion stability can also be assessed by the following method. An oil-in-water emulsion was produced with a range of gum product concentrations (e.g., 0.2, 0.5 and 0.7% (w/v)):

| gum (g) | 0.1 | 0.25 | 0.35 |
|---|---|---|---|
| oil (ml) | 10.00 | 10.00 | 10.00 |
| water (ml) | 40.00 | 40.00 | 40.00 |
| Total | 50.00 | 50.00 | 40.00 |

The gum product was dissolved in water using the ultraturrax (John Morris Scientific Equipment) at a setting of 4. Oil (Crisco, polyunsaturated blend) was then added while mixing and held at setting 4 for 45 seconds. The solution was further mixed at setting 8 for 45 seconds. The emulsion obtained was poured into 50 ml measuring cylinders (21 mm internal diameter), sealed with aluminum foil and stored at 27° C. It was then observed for up to a week. Creaming or separation was expressed in percentage volume.

The volume of oil can be varied to provide an HLB in the emulsion that is typical for the intended application.

For measuring the stability of a water in oil emulsion comprising a cultured plant cell gum, ASTM method 3707 or an adaptation thereof can be used.

3.B. —Viscosity Testing

The flow behavior of the gum product in aqueous solutions or mixtures was assessed over a range of gum concentrations, temperatures and shear rates. The gum product was dissolved in water using the ultraturrax at setting number 4. The solution was then stirred and heated to 60° C. Viscosity was measured at decreasing temperatures from 60° to 10° C. using an Epprecht Rheometer (Contraves AG Zurich) at various shear rates. Results were plotted as viscosity versus temperature for different shear rates.

Viscosity plotted as a function of shear rate indicates the thixotropic nature of the gum. Thixotropic profiles indicate whether a gum is suited for particular applications where shear thinning is required (e.g., in drilling muds at the drill bit).

Viscosity plotted as a function of temperature indicates the suitability of the gum as a viscosifier or thickener over the operating temperature range of the intended application.

3.C. —Gel Strength Testing

Gel strength is assessed by measuring rupture strength, shear modulus and back extrusion. Back extrusion is of particular interest because it can distinguish between and characterize soft gels and viscous fluids.

3.C.1—Rupture Strength

Rupture strength is the force required to compress and rupture a gel sample. For rupture strength, the force is proportional to the sample weight.

The gel samples were prepared by mixing *P. communis* gum (0.2–0.5% (w/v)) or *N. plumbaginofolia* (0.5–1.0% (w/v)) in water in 50 mm plastic petri dishes and storing them at 15° C. overnight. Rupture strength was measured by compression on the Instron 1122, using a probe of 150 mm in diameter at a cross-head speed of 50 mm/min.

3.C.2—Shear Modulus

Shear modulus is a measure of the force required to shear/cut the gel. Shear modulus is expressed as stress divided by strain. For shear modulus, the force is proportional to the sample weight.

The gel samples were prepared as in C.1 in a 24 mm diameter glass vial and stored at 15° C. overnight. Shear force was measured on a modified puncture strength meter (Oakenfull, D. G. et al. (1987) "A method for determining the absolute shear modulus of a gel from a compression test" in Gums and Stabilizers for the Food Industry, Vol 4, Phillips, G. O. et al. (eds.) IRL Press, Oxford) with a probe of 3 mm in diameter at the cross head speed of 5 mm/min for 20 seconds. Shear modulus was then calculated using a mathematical model set forth in Oakenfull, D. G. et al. (1987).

3.C.3—Back-extrusion

Back-extrusion force is the force required to compress and shear a gel sample. In back-extrusion, force is independent of sample weight.

The gel samples were prepared as in C.1 in 200 ml beakers of 64 mm and stored at 15° C. overnight. Back-extrusion was performed on the Instron 1122 by plunging a probe of 60 mm in diameter at a speed of 100 mm/min to a depth of 50% into the gel.

3.C.4.—Effective Temperature Range of Gel: Determination of melting and setting points The melting point is determined by observing the temperature at which a 10 ml gel begins to melt in a 11 mm diameter spectrophotometric tube. The determination was aided by observing small glass beads (0.08 g) sinking into the melting gel. As there can be temperature gradients within the gel, a melting range can be observed. The experiment was carried out in a Thermoline waterbath in 5° C. steps.

The setting point was determined by observation of gelling in spectrophotometer tubes. The gel samples in the tubes were stored overnight (18 hours) at a range of temperatures, and the tubes were then inverted to observe if setting had occurred. The temperatures tested were 60°, 10°, 15°, 20°, 25°, 27°, 30°, 37.2° and 45° C.

3.D.—Encapsulating capacity

Encapsulating capacity can be assessed by evaluating a gum-containing spray dried emulsion in terms of flow characteristics and stability, as described in Example 3 of a U.S. Patent application entitled "Plant Gum Material and Use Thereof in Food Products," and filed on even date herewith.

3.E.—Adhesive capacity

Adhesive capacity can be measured by using standard methods such as ASTM (American Society for Testing Materials) method D1713 ("Bonding Permanancy of Water- or Solvent-Soluble Liquid Adhesives for Automatic Machine Sealing Top Flaps of Fiberboard Specimens") and D1581 ("Bonding Permanancy of Water-or Solvent-Soluble Liquid Adhesives for Labelling Glass Bottles"), or adaptations thereof.

Example 4

Papermaking: Preparation of Paper Hand Sheets

A superior strength paper can be produced using the procedure described in Australian Standard 1301 APPITA P203s/80 by adding *N. plumbaginifolia* gum product at the wet end to improve the physical properties of the dry sheet. The observed improvements include increased paper strength (both burst and tensile), greater resistance to erasure, reduced "fuzz" or lint on the paper surface and reduced rate of water penetration as compared to hand sheets prepared without a gum beater aid. The gum product allows for a retention of wet strength and improved yield by providing a more uniform distribution of fines.

The following method (Australian Standard 1301 APPITA P203s/80) was used for the preparation of hand sheets:

Commencing with wood fibre pulp (sourced as chemically treated pulp, semi-chemical pulp, or mechanical pulp or recycled pulp), the gum product was dissolved in a quantity of water sufficient to produce a 2% solids solution. One liter of the dissolved solution was added to 4 liters of pulp placed in a container. Adequate mixing was ensured by sparging for at least 15 minutes. A sample of 500 ml was then place into a larger tapering 15 liter vessel with a 60 mesh screen at the base 100 mm in diameter. A further 10 liters of processed water was added and the mixture was sparged from the base of the vessel for at least 15 seconds to ensure thorough mixing. The base valve was then opened, allowing processed water to drain away, retaining all of the fibers on the wire mesh screen. The base screen was removed from the unit base and covered with a blotter, allowing the wet fibrous mat to be retained by the blotter. Successive cycles produce a number of samples which are then stacked and pressed in a stack to remove excess water. They were then placed in a drying cabinet and maintained at a standard 23° C., 50% relative humidity until testing.

Testing revealed that the subject gum-containing paper has superior tensile strength, stretch, work to rupture and extensional stiffness on an Alweitron Universal Testing machine. Methods for testing paper are known in the art and include, e.g., Australian Standard 1301.403s-89 for "Bursting Strength of Paper;" Australian Standard Appita P404s-81 for "Tensile Strength of Paper and Paperboard;" Australian Standard 1301.419s-89 for "Water Vapour Transmission Rate of Paper;" Australian Standard 1301.411s-89 for "Water Absorptiveness of Paper and Paperboard (Cobb Test);" and Australian Standard Appita P406m-86 for "Bending Quality of Paperboard."

Example 5

Adhesives: Preparation of re-moistenable adhesive

A satisfactory adhesive for envelopes, labels, stamps and aluminum foil sheets, which is of the water re-moistenable type, was prepared as follows:

| 1. | *N. plumbaginifolia* (BLM carbon source) | 1000 gm |
| 2. | Sodium Chloride | 20.5 gm |
| 3. | Glycerol | 20.5 gm |
| 4. | Potato starch | 20 gm |
| 5. | Water | 1300 ml |
| 6. | Preservative | 1 gm |

The water was placed in a high speed mixer and mixing was begun at a slow speed. The gum product was slowly added, allowing it to fully dissolve in the mixing process. After 4 minutes, the sodium chloride, glycerol, starch and preservative were added. After thorough mixing, the mixture was left to stand for 1½ hours.

This produced an adhesive which was applied to the surface of paper and dried. It remained inactive until moisture was reapplied. It was found to be a superior gum for use in these applications as it has good affinity for water and does not cause discoloration of the paper or become brittle on aging. It was found that the adhesive glued pieces of aluminum foil to paper very firmly and also glued pieces of paper together in a manner similar to commercial adhesive pastes.

Example 6

Oil and Gas Well Applications: Preparation of Drilling Mud

A satisfactory drilling mud or fluid can be prepared in stirred tanks as follows:

A large 1,000 liter tank was filled with water. About 6% by weight bentonite (montmorillonite) was added while stirring slowly and continuously until dissolved. In a second 1,000 liter tank filled with water, about 3% by weight *N. plumbaginifolia* gum product was added while stirring slowly until dissolved. In a third holding tank, equal quantities of gum product mixture and bentonite mixture were mixed. This produced a basic drilling fluid to which was added up to 30% solids of barium sulphate or 30% chalk as weighting agents depending upon the nature of the surrounding rock structure. If desired, a biocide can be added to prevent fermentation during storage or down-hole.

The resulting drilling fluid has increased viscosity, and can provide an improved flow of material from the bit to the surface and a uniform dispersion of the solids, thereby acting as a protective colloid. It can also lubricate and reduce fluid loss into porous rock. The resulting drilling fluid is particularly efficacious in providing a uniform suspension and maintaining a consistent fluid in drilling through shale layers, broken rock that has been stabilized, or magnesium or calcium containing rock. During cementing, a stabilizing fluid containing the subject gum product will also have reduced fluid loss.

The *N. plumbaginifolia* gum product, when in an aqueous dispersion with calcium, possesses gelling properties. Such gelling properties can enhance suspension of solids in a drilling mud even when flow has stopped.

Example 7

Printing Applications 7.A. Preparation of Printing Ink

A satisfactory emulsion or suspension water-based flexo ink for printing was prepared using the *N. plumbaginifolia* gum product as a suspension agent to provide uniform dispersion of the pigment elements and prevent the ink from separating. To a typical ink formulation of:

1. Carbon Black
2. Mineral Oil
3. Sodium silicate
4. Sodium carbonate

5. Water was added about 2% by weight of gum product to produce a fine uniform stable suspension of the solid ingredients. Using a high speed mixer running at low speeds the gum product was added to the mixture until thoroughly dispersed. The emulsion mixture was left to stand for 1½ hours prior to use.

7.B. Preparation of a Lithography Fountain solution

The *N. plumbaginifolia* gum product provides a satisfactory substitute for gum arabic in several lithography solutions or mixtures including the plate sensitizer solution, the fountain solution and the protecting solution (used during plate storage). The gum product imparts good wettability particularly to the fountain solution. It also supplies the viscosity required to allow the fountain solution to cling to the plate without running off or forming isolated droplets or pools on the plate.

A fountain solution was prepared as follows:

| 1. | Water | 700 ml |
|---|---|---|
| 2. | Propylene Glycol | 50 ml |
| 3. | Biocide Parabens (methyl/ethyl-hydroxy parabenzoic acid at 0.5–2.0% (w/v) in water adjusted to pH 7.0 with phosphate buffer | 1 ml |
| 4. | gum product solution 3% (w/w) | 200 ml |
| 5. | pH buffer | 40 ml |

All ingredients other than the gum product solution were added to a mixture, and stirred until dispersed (10 mins). The gum product solution was then added, and stirring was continued.

The mixture was then allowed to stand for 30 minutes before use.

7.C. Comparison of *N. Plumbaginifolia* gum to gum arabic in fountain solutions

The following formulae were made up by Cetec Pty. Ltd., a consultant. All values (except pH) are w/w percent.

|  | F1 | F2 | F3 | F4 |
|---|---|---|---|---|
| Water | 70 | 90 | 70 | 90 |
| Propylene Glycol | 5 | — | 5 | 5 |
| 3% w/w gum arabic soln. | 15–20 | — | — | — |
| biocide | 0.1 | 0.1 | 0.1 | 0.1 |
| pH buffer (phosphate) | pH 5–7 | pH 5 | pH 5–7 | pH 5 |
| Phosphoric acid | — | 2 | — | 2 |
| gum arabic EDTA | — | 2 | — | 2 |
| EDTA | — | 0.5 | — | 0.5 |
| *N. plumbaginifolia* gum 3% w/v | — | — | 0.3–0.4 | — |
| *N. plumbaginofolia* gum | — | — | — | 0.3–0.4 |

F1 and F2 are standard fountain solutions that employ gum arabic. F3 and F4 are identical to F1 and F2, respectively, except that *N. plumbaginifolia* gum product has been substituted for the gum arabic in a weight that is 1/50 of the gum arabic weight.

When these fountain solutions were employed in an offset litho printing, it was found that the *N. plumbaginifolia* gum product performed comparably to the gum arabic fountain solutions in terms of ink-plate roll up and in degree of plate background desensitization. The plate wetting characteristics of the two products were also very similar. The *N. plumbaginifolia* gum was found to be less soluble in isopropyl alcohol than gum arabic; since isopropanol is very widely used as part of the dampening system of modern, fast lithographic offset presses, this may be a negative feature.

Example 8
Fabric Printing: Preparation and use of reactive dyestuff for wool or cotton Satisfactory dyeing of wool and cotton was accomplished as follows:

First, a thickening was prepared:

| 1. | *N. plumbaginifolia* gum product | 150 gm |
|---|---|---|
| 2. | Cold water | 2800 ml |
| 3. | Sodium metaphosphate (Calgon ™) | 30 gm |

The water was agitated with a high speed mixer during gradual addition of the sodium metaphosphate. The gum product was then added slowly, but fast enough so that all the powder was added before the viscosity has risen appreciably. Stirring was continued for 5–10 minutes until all particles were swollen and had formed a thick suspension. The mixture was allowed to stand for 1½ hours.

Then the following were added:

| 4. | Diphasol ™ solution | 115 ml |
|---|---|---|
| 5. | Hot water | 975 ml |
| 6. | White spirit | 3750 ml |
| 7. | Resist salt L ™ | 150 gm |

The thickening mixture was then stirred in the high speed mixer for 20 minutes.

The screen printing paste was prepared by mixing the following:

| 1. | Dyestuff | 3 gm |
|---|---|---|
| 2. | Urea | 10 gm |
| 3. | Hot to boiling water | 30 ml |
| 4. | Thickening (as above) | 50 gm |
| 5. | Sodium bicarbonate | 4 gm |

Using a high speed mixer, the dyestuff and urea were thoroughly dry mixed. Then the hot water and thickening were added and mixed.

The printing paste was used in a standard fabric screen printing method. The printed cotton and wool were then dried followed by steaming for 8 minutes. They were then rinsed thoroughly in cold water followed by a soaping at or near the boiling point with a detergent solution of Lissapol ND (2% w/w solution) and finally rinsed in cold water. The printing on the wool and cotton material appeared stable.

Example 9
Paints
9.A. Preparation of Acrylic Resin Paint

A stable water emulsion was prepared using the following formulations:

Premix in a ball mill:

| 1. | Tap water | 125 ml |
|---|---|---|
| 2. | Daxad 30 ™ Dispersant | 8 gm |
| 3. | Tergitol NPX ™ Surfactant | 4 ml |
| 4. | Victawet 35B ™ Wetting Agent | 2.5 ml |

Then the mill speed was increased and the following was added slowly:

| 5. | Chemacoil TA-1001 ™ Resin | 74 gm |
|---|---|---|

The speed was adjusted to disperse the following pigments and additives:

| 6. Zinc oxide AZO-ZZZ-33 ™ | 75 gm |
| 7. Titanox RANC ™ Rutile Titanium Dioxide | 175 gm |
| 8. Titanox A168L0 ™ Anatase Titanium Dioxide | 25 gm |
| 9. Asbestine 3X ™ Talc | 100 gm |
| 10. Ethylene Glycol | 18.5 gm |
| 11. Nuodex PMA-18 Mildewoide ™ | 3 gm |
| 12. Nopco NDW ™ Defoamer | 4 gm |

The mill was then slowed to mixing speed.

| 13. N. plumbaginifolia gum product emulsion (2% w/w aqueous solution) | 165 ml |
| 14. Rhoplex AC-34 ™ Acrylic Emulsion | 372 gm |
| 15. Super Cobalt ™ Drier | 1 gm |

Mixing continued for at least ½ hour at mixing speed. Other pigments, such as carbon black or red oxide of iron, may be added to this to replace part of the titanium dioxide ingredients in items 7 & 8 and provide a differing color balance. The above formulation was derived from Ernest Flick "Water-Based Paint Formulations" Noyes Publications, Parkridge, N.J.

9 B. Oil Emulsion Paint

A satisfactory thixotropic paint was prepared as follows. Premix in a high speed stone mill:

| 1. Water | 205 ml |
| 2. Victawet 35B ™ Wetting agent | 4 ml |
| 3. Potassium polyphosphate | 5 gm |

Adjust speed of the mill to disperse the following additives and pigments:

| 4. Ethylene glycol | 10 gm |
| 5. Titanox RANC ™ Rutile TiO₂ | 175 gm |
| 6. Titanox A168L0 ™ Anatase TiO₂ | 50 gm |
| 7. Asbestine 3X ™ Talc | 50 gm |
| 8. Zinc oxide AZO-ZZZ-33 ™ | 125 gm |
| 9. Nuodex PMA-18 Mildewoide ™ | 2 ml |
| 10. Nopco NDW ™ Defoamer | 2 ml |
| 11. Victawet 35B ™ Wetting agent | 16 gm |

The mill was then slowed to mixing speed and the following were added:

| 12. N. plumbaginifolia emulsion (2.5% w/w) | 130 ml |
| 13. Emulsified linseed oil (60% solids) | 340 ml |
| 14. Super Cobalt ™ drier | 11 gm |

Milling was continued for approximately ½ hour.

This procedure resulted in a paint that tends to set to relatively stiff or "buttery" consistency upon standing, but thins down to relatively mobile liquid when mechanically agitated. This thixotropic character is such that the shearing action of the brush used to apply the paint to a surface is sufficient to render the paint adequately mobile. The paint leaving the brush remains fluid for a sufficient time to bring about good levelling (i.e., the brush marks disappear while the paint again sets to a stiff consistency before it has time to run appreciably on the surface painted).

This thixotropic property in paints is valuable in flat paints meant to be applied to interiors with a brush because it prevents the running of the paint and at the same time eliminates brush marks. Thixotropic paints possess a further advantage quite apart from their intended use for the reason above, in that the paint acquires a buttery or solid consistency upon standing in containers. Segregation or stratification of the paint during long periods of storage is thus prevented.

The above formulation and methods were derived from U.S. Pat. No. 2,135,936, Nov. 8, 1938, for "Use of gum arabic in paint" and from "Emulsion and Water Soluble Paints and Coatings."

Example 10
Ceramic Glazes

The suspension of the glaze ingredients in a glaze slip for several hours or even days has been achieved using N. plumbaginifolia gum product as an emulsifying and/or suspending agent. Further, the resulting glaze has superior clarity and stability.

A stable glaze slip was prepared as follows:

To prepare an emulsifying/stabilizing mixture, the following were combined:

| 1. N. plumbaginifolia dry gum product (grown on BLM as carbon source) | 10 gm |
| 2. Cold water | 500 cc |

Example 11
Clear Thixotropic Detergent or Cleaning Preparation

A satisfactory thixotropic cleaning detergent with superior grip and film forming properties was prepared as follows:

| 1. Water | 812 ml |
| 2. N. plumbaginifolia (BLM carbon source) | 40 gm |
| 3. Sodium chloride | 20 gm |

The gum product was added to the water in a high speed mixer running at a slow speed and was mixed for 15 minutes. The mixture was then left for 1½ hours and the sodium chloride was added, mixing slowly for 3–5 minutes. Sodium ethylsulphate was then added while mixing continued:

| 4. Sodium ethylsulphate (C12-14 2E.0.) (100% basis) | 125 gm |
| 5. Perfume | <.5 gm |
| 6. Dye | <.5 gm |
| 7. Preservative | <.5 gm |

The perfume, dye and preservative were then added, and mixing continued for another 10 minutes.

Because the foregoing formulation does not contain either ethyl alcohol or propylene glycol (which can be used in cleaning detergents), the possibility of precipitation of the gum due to a high alcohol concentration is averted.

The resulting product is a clear cleaning agent which tends to be relatively stiff and provides an adequate detergent which clings to the surfaces. This is a desirable characteristic particularly in the cleaning of vertical surfaces. It was found that the BLM carbon source enhanced the film forming properties of the detergent.

Example 12
Cosmetic Creams and Lotions

12.A. The concentrated gum from Nicotiana Batch 3–1000 (1.7% total solids) was found to have pleasant soft feeling on the skin and to dry without stickiness. When mixed with water, it makes a satisfying, i.e., moisturizing, skin treatment without any further additions. Another product was prepared by perfuming the biopolymer solution with 0.1% v/v rose oil.

12.B. A cosmetic lotion was prepared with the ingredients indicated below. The vegetable oil, perfuming oil and glycerol were added to the biopolymer solution while mixing with a high speed stirrer such as an Ultraturrax at a setting of about 6.

| Nicotiana gum #3-1000 | 2.4% (w/w in H₂O) |
| Orange oil | 1.0% (w/w) |
| Olive oil | 2.3% (w/w) |
| Glycerol | 5.3% (w/w) |

The Nicotiana gum was mixed in the water in a high speed stirrer such as an Ultraturrax at a setting of about 6. The olive oil, orange oil and glycerol were then added. The result was a soft gel with a pleasant fresh aroma which can be spread on the hands or face, leaving skin feeling fresh and soft.

12.C. A cosmetic lotion was prepared using the following:

| Nicotiana gum #3-1000 | 1.7% (w/w in H₂O) |
| Sunflower oil | 1.3% |
| Glycerol | 4.0% |

The ingredients were combined as in 11.B. The resulting product was soft enough to be used in a pump-action dispenser. A perfuming oil can be added if desired.

12.D. Other batches of gum from other cell lines were used to prepare products with different properties. For example, a cream was prepared from gum produced by Nicotiana cells growing in a medium containing Brewers Liquid Maltose ("BLM") 162 g/liter, as the source of sugar. The resulting gum produced a viscous solution and was used to prepare a lotion with the following formulation:

| Nicotiana gum | 2.3% (w/w in H₂O) |
| Peanut oil | 3.3% |
| Rose oil | 0.1% |
| Glycerol | 5.0% |

Example 13
Compositions and Selected Rheological Properties of Plant Cell Gums Tables 3 and 4 list relative weight proportions of protein and ash and types of polysaccharide in plant cell gums obtained from suspension cultures of a variety of vascular plants including both dicots (Table 3) and monocots (Table 4). Table 5 lists explant sources and culturing conditions for the plant cell cultures of Tables 3 and 4 and Table 6 lists the maximum polysaccharide concentration obtained in cultures during growth cycle measurements.

There is significant variation in the amount of protein+ ash, from a low of about 12% for Timothy Grass to a high of 58% for white clover, in the representative plant cell gums exemplified. Xyloglucan is relatively low in the gums of cells of Fabaceae and Poacea but relatively high in pig face and Malvaceae plant cell gums. Arabinogalactan which will be attached to protein also varies significantly from a high of 28% to a low of 10%. Heteroxylan is only significant in cells of monocots. Glucuronomannan is high in the monocot Poacea but also in Nicotiana plumbaginifolia plant cell gum. Rhamnogalacturonan is also variable among the gums assessed.

The percentages by weight of the components measured add up approximately to 100% for each cell line. Discrepancies in total weight percent may occur due to the inherent errors in analytical techniques or if the assumptions made with respect to the structures of polysaccharides present are inaccurate. For example, the presence of minor functional groups such as methyl or acetyl groups may not be taken into account. The relative amounts of individual polysaccharides is inferred from detailed methylation data from isolated gum.

Methylation analysis was performed using analytical methods well-known in the art. Protein and ash were also measured using standard methods well-known in the art. Briefly, total nitrogen (N) was determined using the Kjeldahl method and expressed as protein (N×6.25). Inorganic material (ash) was determined by ash content. Monosaccharide compositions were determined by GC/MS following carboxyl reduction and methylation analysis. Isolated gums were carboxyl reduced and methylated and the partially methylated alditol acetates were analyzed by GC-MS.

The proportions of individual polysaccharides present in the gum were determined based on characteristic linkage structures of purified polymers from dicotyledonous and monocotyledonous species as described by Shea et al. (1989) Planta 179:293. Xyloglucan was the sum of 4,6-Glc and terminal Xyl equal to 4,6-Glc, as well as 2-Xyl, 2-Gal, terminal Fuc and 4-Glc equal to one third that of 4,6-Glc, except for *Solanum tuberosum* and *Lycopersicon esculentum* in which the structure of xyloglucan from *S. tubersum* was used as a model (Ring and Selvendran (1981)). Galactoglucomannan was the sum of 4-Man and 4,6-Man, 4-Glc equal to the sum of these Man linkages and terminal Gal equal to 4,6-Man. Glucomannan was the sum of 4-Man and any 4-Glc not assigned to xyloglucan. 3,6-Arabinogalactans (type II) were the sum of 3-Gal, 6-Gal, and 3,6-Gal and terminal Ara equal to 3,6-Gal. Heteroxylans were the sum of 4-Xyl, 2,4-Xyl,and 3,4-Xyl and terminal GlcA and terminal Ara equal to 2,4-Xyl and 3,4-Xyl. 4-Galactan was the sum of 4-Gal and 2,4-Gal and terminal Gal equal to 2,4-Gal, Arabinan was the sum of 2-Ara, 3-Ara, 5-Ara, 2,5-Ara and terminal Ara equal to 2,5-Ara. Glucuronomannan was the sum of 2-Man, 2,3-Man and 4-GlcA, 3,4-GlcA and terminal Ara and terminal Gal equal to the sum of 2,3-Man and 3,4-GlcA. Galacturonan was the sum of 4-GalA, 4-GalA (6–0-Me) and 3,4-GalA, and rhamnogalacturonan was the sum of these linkages and 2,4-Rha.

Suspension cultures were initiated from explants indicated in Table 6 generally following the methods described in Example 2 except that different media, hormone balance (as indicated in Tables 5 and 6) and fermentation times were used. Suspension cultures were grown in 2 L shake flasks shaken at 100 rpm at 27° C. in the dark.

Table 6 lists gum yield produced by suspension cultures. Gum production in these cell lines has not as yet been optimized by variation of fermentation conditions and media components. Increased yields of gum can be achieved by such optimization methods.

Tables 3 and 4 compare emulsification, gelling and the viscosity of various dicot and monocot plant cell gums. Gums were isolated essentially as described in example 2.

Emulsification was tested by determining the droplet size of a limonene emulsion formed using 1% (w/v) of an aqueous gum solution essentially as described in example 3. Pig face gum gave an excellent emulsion with droplet size of 4.8 µm which is three to five times smaller than emulsion droplets formed using Nicotiana and Pyrus gum, respectively. Gums which can generate an emulsion with droplet size less than about 50µm are particularly useful in the drink industry.

Viscosity was measured essentially as described in example 3B. Some of the gums including Timothy Grass and millet appear to be viscoelastic, i.e., displaying both solid-like (elastic) and liquid-like (viscous) properties. Viscoelastic properties are time dependent. A viscoelastic material can exhibit either linear or non-linear viscoelastic behavior. Viscoelastic behavior can be observed, for example, by rapidly twisting a bottle of gum and watching recoil. Linear viscoelastic behavior is observed at low strain (non-destructive testing). Measurements of storage modulus (G') and loss modulus (G"), both well-known measurements, give an indication of the amount of solid-like behavior (G') and liquid behavior (G").

Pig face gum has a relatively low viscosity combined with the capability to form low droplet size emulsions. Pig face gum is thus useful in emulsification applications and particularly well-suited for use in cloud emulsions. Cloud emulsions have applications in the food industry, for example for manufacture of soft drinks, and in the chemical industry and agriculture for preparation of chemical emulsions including emulsions of agricultural chemicals (pesticides, etc.).

Timothy Grass gum displays good gelling ability and high viscosity. This gum is useful in applications where there is a need to suspend or stabilize or where water-holding properties are needed. This gum has application, among many others, in the food industry for ice cream and dessert items and in the preparation of spray emulsions, for example, for agricultural chemicals.

Millet gum has high viscosity associated with water thickening properties. In addition to a variety of uses in the food industry in sauces, bakery glaces and other foods, millet gum has application in the preparation of drilling muds.

Derek Morton "Determination of Primary Structure of Microbial Polysaccharides", Ohio Food Hyrocolloids Conference, September 1994, provides an exemplary listing of applications and specific industrial uses for gum having a given rheological property or characteristic.

Example 14
Additional Media for Plant Cell Cultures
Linsmaier and Skoog Powder (LS) Medium for Chicory

| LS Powder | 4.16 g |
|---|---|
| Sucrose | 30.0 g |
| Organics stock | 1.0 ml |
| 2,4-D (0.1 mg/ml) | 2.2 ml |
| NAA (0.2 mg/ml) | 0.186 ml |

Dissolve all ingredients, except agar, in 800 ml Milli-Q water. Adjust pH to 6.0 with KOH and make up to 1 L. Add agar 5.0 g if making solid medium. Autoclave for 20 m at 121° C.

Organic Stock

| Thiamine Hydrochloride | 40 mg |
|---|---|

Dissolve both ingredients and make up to 100 ml with Milli-Q water and use stock at 1 ml/L. Aliquot into 10 ml portions and freeze.

Tomato BAL Medium

Add concentrated stock solutions and sucrose to approximately 900ml of Milli-Q water with constant agitation using a magnetic stirrer:

| Macro elements | 10 ml |
|---|---|
| Micro elements | 1 ml |
| Vitamins | 1 ml |
| $CaCl_2$ | 2.6 ml |
| $KH_2PO_4$ | 10 ml |
| Fe.EDTA | 1 ml |
| 2iP | 1 ml |
| 2,4-D | 20 ml |
| KI | 0.5 ml |
| Sucrose | 30 g |

Macro and micro elements and vitamins are the same as used in pear BAL. Adjust pH to 5.0–6.0 with KOH (0.1 or 1M) and adjust final volume to 1 liter. For solid medium add 0.5% agar (5 g/L) after adjusting Ph and volume. Sterilize for 20 m at 10 psi (116° C.).

TB1 Medium for Tuberose (PETAL)

| LS powder | 4.60 g |
|---|---|
| Sucrose | 30.0 g |
| 2,4-D | 20.0 ml (Stock Solution 0.1 mg/L) |

Dissolve all ingredients in approximately 800 ml Milli-Q water and then make up to 1 L. Adjust pH to 5.8–6.0 with 0.1M KOH. To prepare solid medium, add 5.0 g of agar to a 2 L flask, add dissolved consitutents and steam until dissolved. Sterilize at 10 psi for 20 m.

A related medium TB2 (Tuberose 2) also used for petal culture is prepared in a similar manner but contains ⅟10 th the amount of 2,4-D (i.e., add 2.0 ml of the Stock Solution of 2,4-D rather than 20 ml).

TABLE 3

COMPOSITION AND SELECTED PROPERTIES OF PLANT CELL GUMS OF DICOTS

| | RELATIVE PROPORTION (%)[1] Dicotyledons | | | | | | | |
|---|---|---|---|---|---|---|---|---|
| | Caryophyllidae | Dilleniidae | | | Rosidae | | | |
| | Aizoacea | | Malvaceae | | Roseace | Fabaceae | | |
| | Mesembrya- nthemum chilense pig face | Actinidiaceae Actinidia deliciosa Kiwi fruit | Hibiscus esculentus okra | Sida rhombifolia Paddy's lucern | Pyrus[2] communis brown pear | Medicago sativa alfalfa | Trifolium repens white clover | Trifolium pretense red clover |
| Protein & Ash | 26 | 41 | 30 | 52 | 28 | 41 | 58 | 48 |
| Xyloglucan | 27 | 21 | 18 | 14 | 17 | 7 | 4 | 5 |
| Galactoglucomannan | — | 6 | — | — | — | — | — | — |
| Glucomannan | — | — | — | 3 | — | — | 3 | 5 |
| 3,6-Arabinogalactan (Type II) | 18 | 21 | 17 | 23 | 30 | 27 | 23 | 16 |
| Heteroxylan | tr | 2 | 1 | 2 | 2 | 2 | 2 | 1 |
| 4-Galactan (Type I) | 1 | — | — | — | — | — | — | — |
| Arabinan | 4 | 1 | 1 | 2 | 7 | 5 | 3 | 7 |
| Glucuronomannan | — | — | — | — | 4 | — | — | 11 |
| *Rhamnogalacturonan Galacturonan* | 19 | 8 | 36 | 3 | 6 | 9 | 5 | 6 |
| SELECTED PROPERTIES OF GUMS: | | | | | | | | |
| Emulsification[3] 1% Gum | 4.8 | NT | 56.0 | NT | 27.0 | NT | NT | NT |
| Gelling 1% Gum[4] | NO | NA | NO | NA | NO | NT | NT | NT |
| Viscosity[5]: | | | | | | | | |
| 1/S | 11.0 | NT | — | NT | 129.0 | NT | NT | NT |
| 100/S | 6.8 | NT | 2.5 | NT | 19.0 | NT | NT | NT |

| | RELATIVE PROPORTION (%)[1] Dicotyledons Asteriade | | | |
|---|---|---|---|---|
| | Solanaceae | | | Asteracae |
| | Solenum tuberosum potato | Lycopersicon esculentum tomato | Nicotiana plumbaginifolia ornamental tobacco | Cichorium intybus chicory |
| Protein & Ash | 49 | 38 | 10 | 52 |
| Xyloglucan | 15 | 9 | 32 | 5 |
| Galactoglucomannan | 12 | 10 | 13 | — |
| Glucomannan | — | — | — | 3 |
| 3,6-Arabinogalactan (Type II) | 14 | 16 | 10 | 20 |
| Heteroxylan | 3 | 1 | 1 | 1 |
| 4-Galactan (Type I) | — | — | — | 1 |
| Arabinan | 2 | 1 | — | 3 |
| Glucuronomannan | — | — | 22 | — |
| *Rhamnogalacturonan Galacturonan* | 3 | 22 | 13 | 14 |
| SELECTED PROPERTIES OF GUMS: | | | | |
| Emulsification[3] 1% Gum | NT | 32.0 | 15.0 | NT |
| Gelling 1% Gum[4] | NT | NO | NO | NT |

TABLE 3-continued

COMPOSITION AND SELECTED PROPERTIES OF PLANT CELL GUMS OF DICOTS

| | | | | |
|---|---|---|---|---|
| Viscosity[5]: | | | | |
| 1/S | NT | 67.0 | 140.0 | NT |
| 100/S | NT | 19.0 | 55.0 | NT |

[1]Calculated as the sum of mol % of individual monosaccharide residues; tr = trace amount; The percentages of components listed add up to approximately 100% for each cell line; Variations of the total from 100% occur because the assumptions of structures of polysaccharides present may be inaccurate such that the presence of minor functional groups such as methyl or acetyl groups may not have been taken into account.
[2]Brown pear is distinct from green pear described in Example 1.C.
[3]Droplet size measured in μm
[4]YES means that a semi-solid structure indicative of gelling was visually observed; NO means no such semi-solid structure was observed.
[5]Viscosity is given in centipoise, and measured as a function of sheer rate in reciprocal seconds.

TABLE 4

COMPOSITION AND SELECTED PROPERTIES OF PLANT CELL GUMS OF MONOCOTS RELATIVE PROPORTIONS (%)[1]

| | Monocotyledons | | |
|---|---|---|---|
| | Commelinidae Poaceae | | |
| | *Phleum pratense* Timothy grass | *Panicum miliaceum* millet | Liliiade Agavaceae *Polianthes tuberosa* |
| Protein & Ash | 14 | 39 | 51 |
| Xyloglucan | 5 | 3 | 3 |
| Galactoglucomannan | — | — | — |
| Glucomannan | — | 6 | 15 |
| 3,6-Arabinogalactan (Type II) | 28 | 6 | 20 |
| Heteroxylan | 11 | 7 | 6 |
| 4-Galactan (Type I) | 1 | 7 | — |
| Arabinan | 4 | 3 | 2 |
| Glucuronomannan | 19 | 12 | — |
| Rhamnogalacturonan | tr | tr | 1 |
| Galacturonan | | | |
| SELECTED GUM PROPERTIES: | | | |
| Emulsification[2] (1% Gum) | 20.0 | 17.0 | |
| Gelling[3] (1% Gum) | YES | NO | |
| Viscosity[4]: | | | |
| 1/S | 4500 | 1800 | |
| 100/S | 150.0 | 25.0 | |

[1]Calculated as the sum of the mol % of individual monosaccharide residues; tr = trace amount; The percentages of components listed add up to approximately 100% for each cell line; Variations of the total from 100% occur because the assumptions of structures of polysaccharides present may be inaccurate such that the presence of minor functional groups such as methyl or acetyl groups may not have been taken into account.
[2]Droplet size measured in μm.
[3]YES means that a semi-solid structure indicative of gelling was visually observed; No means no such semi-solid structure was observed.
[4]Viscosity is given in centipoise, and measured as a function of shear rate in reciprocal seconds.

TABLE 5

Plant cell suspension cultures: Explant Source and Culturing Conditions

| Species | Explant | Medium[1] | No. sub-cultures (callus)[2] | No. sub-cultures (suspension) | Age of culture at harvest (days) |
|---|---|---|---|---|---|
| Dicots | | | | | |
| Caryophyllidae Aizoaceae *Mesembryanthemum chilense* | leaf | MS2 | 25 | 6 | 13 |
| Dilleniidae Actinidiaceae *Actinidia deliciosa* | fruit with seed | MS9 | 10+ | 4 | 21 |
| Malvaceae | | | | | |
| *Hibiscus esulentus* | seedling stem | MS9 | 7 | 4 | 13 |
| *Sida rhomifolia* | seedling stem | MS9 | 20 | 4 | 14 |
| Rosidae Rosaceae *Pyrus communis*[3] | fruit | pear BAL | 24 | 7 | 11 |
| Fabaceae | | | | | |
| *Medicago sativa* | seed | MS1 + NOA | 20+ | 3 | 6 |
| *Trifolium repens* | seed | MS9 | 10+ | 3 | 14 |
| *Trifolium pratense* | seed | MS6 | 0 | 3 | 11 |
| Asteridae Solanaceae | | | | | |
| *Solanum tuberosum* | growing points | MS6 | 18 | 5 | 18 |
| *Lycopersicon esculentum* | fruit | tomato BAL | 20+ | 2 | 12 |
| Asteraceae *Cichorium intybus* | DSM-Gmbh[4] | LS | 11+ | 7 | 11 |
| Monocots | | | | | |
| Commelinidae Poaceae | | | | | |
| *Phleum pratense* | seed | MS + 2,4-D[5] | 0 | 3 | 14 |

TABLE 5-continued

Plant cell suspension cultures: Explant Source and Culturing Conditions

| Species | Explant | Medium[1] | No. sub-cultures (callus)[2] | No. sub-cultures (suspension) | Age of culture at harvest (days) |
|---|---|---|---|---|---|
| Panicum miliaceum | seed | MS3/MS9 | 2 | 4 | 14 |
| Lilidae Agavaceae Polianthes tuberosa | leaf | MS17 | 10 | 3 | 18 |

[1]MS1 = MS powder with 0.5 mg/L 2,4-D (2,4,dichlorophenoxyacetic acid);
MS2 = MS powder with 2.0 mg/L 2,4-D;
MS3 = MS powder with 4.0 mg/L 2,4-D;
MS6 = MS powder with 4.0 mg/L 2,4-D and 1.075 mg/L mixed cytokinins;
MS9 = MS powder with 4.0 mg/L 2,4-D and 2.150 mg/L mixed cytokinins;
MS17 = MS powder with 2.0 mg/L NAA (1-naphthaleneacetic acid) and 2.0 mg/L BAP (6-benzylaminopurine);
LS = LS powder with 0.2 mg/L 2,4-D and 0.04 mg/l NAA, see text Example 14; tomato BAL, see text Example 14;
NOA = napthoxyacetic acid used at final concentration 0.5 mg/L;
Concentration of 2,4-D in Phleum pratense culture is 2.0 mg/L
[2]"+" means more, i.e., 10+ means more than 10.
[3]Brown pear.
[4]Commercial source of plant cell culture; Deutsche Sammlung von Mikroorganismen und Zelkulturen.
[5]Millet has been grown on both MS3 and MS9 with substantially the same results. The specific results shown were obtained on MS9.

TABLE 6

Polysaccharide Production in Selected Suspension Cell Cultures

| CELL LINE | EXPLANT | MEDIUM[1] | POLYSACCHARIDE[2] grams/litre |
|---|---|---|---|
| DICOTS | | | |
| Pig Face Mesembryanthemum chilense | leaves | MS2 | 3.1 |
| Kiwi Fruit Actinidia deliciosa syn chinesis | fruit | MS1 | 0.06 |
| Okra Hibiscus esculentis | seedling stem | MS9 | 3.25 |
| Paddy's lucern Sida rhambifolia | seedling stem | MS9 | 0.5 |
| Pear Pyrus communis[3] | fruit | Pear BAL | 3–4 |
| Alfalfa Medicago sativa | seed | MS + NOA | 1.25 |
| White clover Trifolium repens | seeds | MS9 | 0.85 |
| Red clover Trifolium pratense | seeds | MS6 | 1.9 |
| Potato-red Solanum tuberosum | growing points | MS5 and MS6 | 1.0 |
| Tomato Lycopersicon esculentum | fruit | Tomato BAL | 1.75 |
| Nicotiana Nicotiana plumbaginofolia | existing culture[4] | CSV | 3.5–4.5 |
| Chicory Cichorium intybus | DSM-Gmbh[5] | LS | 1.6 |
| Monocots | | | |
| Timothy Grass Phleum pratense | seed | MS + 2,4-D | 6.0 |
| Millet Panicum miliaceum | seeds | MS9 | |
| Tuberose Polyanthes tuberosa | leaf | MS17 | 2.7 |
| Tuberose Polyanthes tuberosa | petal | TB1 | 1.9 |

[1]See footnote 1 Table 5 for media descriptions; CSV see text Example 1.B; TB1 see text Example 14.
[2]The polysaccharide concentration listed is the maximum concentration obtained in growth cycle measurements; Polysaccharide is typically harvested on the culture day on which this maximum occurs; Tuberose petal gum was harvested on day 23.
[3]Brown pear
[4]The Nicotiana plumbaginifolia culture was obtained from Paul Ebert of the School of Botany of the University of Melbourne (February 1989).
[5]Commercial source; Deutsche Sammlung von Mikroorganismem und Zelkulturen.

We claim:

1. A process for manufacturing an industrial, pharmaceutical or cosmetic product, said process excluding food manufacturing, which process comprises a step of including a viscosifying agent, thickening agent, gelling agent, emulsifying agent, suspending agent, stabilizing agent, encapsulating agent, flocculating agent, film-forming agent, sizing agent, adhesive agent, binding or coating agent, lubricating agent, water retention agent or coagulation agent or any combinations of such agents in the manufactured product, wherein a cultured plant cell gum of a vascular plant produced by suspension culture of cells of a plant selected from the group consisting of Nicotiana, Pyrus, Phleum, Lolium, Hibiscus, Lycopersicon, Panicum, Mesembryanthemum, Actindia, Sida, Medicago, Trifolium, Solanum, and Cichorium is used as said agent.

2. The method of claim 1 wherein the cultured plant cell gum is produced by suspension culture of cells of a plant selected from the group consisting of Nicotiana plumbaginafolia, Pyrus communis, Phleum pratense, Hibiscus esculentus, Lycopersicon esculentum, Panicum milliaceum, Actindia deliciosa, Sida rhombifolia, Medicago sativa, Trifolium repens, Trifolium pratense, Solanum tuberosum, and Cichorium intybus.

3. The method of claim 1 wherein the cultured plant cell gum is produced by suspension culture of cells of a plant selected from the group consisting of Nicotiana, Pyrus, Phleum, and Lolium.

4. The method of claim 1 wherein the cultured plant cell gum is produced by suspension culture of cells of a plant selected from the group consisting of Actindia, Sida, Trifolium, and Cichorium.

5. The method of claim 1 wherein the cultured plant cell gum is produced by Phleum pratense cells.

6. The method of claim 1 wherein said gum is employed as an emulsifying agent.

7. The method of claim 6 wherein said gum is produced in suspension culture of Nicotiana plumbaginafolia or Pyrus communis.

8. The method of claim 1 wherein said gum is employed as a viscosifying agent.

9. The method of claim 8 wherein said gum is produced in suspension culture of Phelum pratense.

10. The method of claim 1 wherein said gum is employed as a gelling agent.

11. The method of claim 10 wherein said gum is produced in suspension culture of Phelum pratense.

12. The method of claim 1 wherein said cultured plant cell gum is that of a plant cell line that produces at least about 2.0% (w/v) gum in a final culture broth.

13. The method of claim 1 which is a method of manufacturing a cosmetic wherein said cultured plant cell gum is used without prior purification of gum fractions.

14. The method of claim 13 wherein said cultured plant cell gum is included in said cosmetic product at a concentration ranging from about 0.5% to 4.0% (w/v).

15. The method of claim 1 which is a method of manufacturing a cleaning detergent wherein said cultured plant cell gum is included in said detergent at a concentration ranging from about 1% to 10% (w/v).

16. The method of claim 1 which is a method of manufacturing an adhesive wherein said cultured plant cell gum is included in said adhesive at a concentration ranging from about 1% to 3% (w/v).

17. The method of claim 1 which is a method of manufacturing a paint wherein said cultured plant cell gum is included in said paint at a concentration ranging from about 0.2% to 0.3% (w/v).

18. The method of claim 1 which is a method of manufacturing a dyestuff wherein the cultured plant cell gum is included in said dyestuff at a concentration ranging from about 0.1% to 5.0% (w/v).

19. The method of claim 1 which is a method of manufacturing a printing ink wherein the cultured plant cell gum is included in said ink at a concentration ranging from about 0.5% to 4.0% (w/v).

20. The method of claim 1 which is a method of manufacturing a ceramic glaze or coating wherein the cultured plant cell gum is included in said glaze or coating at a concentration ranging from about 0.05% to 3.0% (w/v).

21. The method of claim 1 which is a lithography method wherein an emulsifying or viscosifying agent is included in a lithography solution and wherein said agent is a cultured plant cell gum included in said lithography solution at a concentration ranging from about 0.01% to 2.0% (w/v).

22. An industrial, pharmaceutical or cosmetic product produced by the method of claim 1.

23. An industrial, pharmaceutical or cosmetic product of claim 22 selected from the group consisting of sheet paper, an adhesive, an oil and gas well fluid, an ink formulation, a lithography solution, a textile, a textile dyestuff, paint, ceramic glaze, cleaning detergent, a cosmetic lotion and a cosmetic cream.

24. The oil and gas well fluid of claim 23, selected from the group consisting of a drilling fluid, a cementing fluid, a completion fluid, and an enhanced oil recovery injection fluid.

25. The oil and gas well fluid of claim 24 comprising a cultured plant cell fermentation mixture.

26. The product of claim 24 wherein said cultured plant cell gum is present in said product at a concentration ranging from about 0.1% to 10% (w/v) dependent upon the application.

27. The lithography solution of claim 23, selected from the group consisting of a fountain solution, a sensitizing solution and a protecting solution.

28. The paint of claim 23 selected from the group consisting of oil emulsion paint and acrylic resin paint.

29. The adhesive of claim 23 comprising from about 1% to 3% (w/v) of said cultured plant cell gum.

30. The cleaning detergent of claim 23 comprising from about 1% to 10% (w/v) of said cultured plant cell gum.

31. The cosmetic of claim 23 comprising from about 0.5% to 4% (w/v) of said cultured plant cell gum.

32. The oil and gas well fluid of claim 23 which comprises from about 0.1% to 3% (w/v) of said cultured plant cell gum.

33. The ink formulation of claim 23 which comprises from about 0.5% to 4% (w/v) of said cultured plant cell gum.

34. The lithography solution of claim 23 which comprises from about 0.01% to 2% (w/v) of said cultured plant cell gum.

35. The dyestuff of claim 23 which comprises from about 0.1% to 5% (w/v) of said cultured plant cell gum.

36. The paint of claim 23 which comprises from about 0.1% to 5% (w/v) of said cultured plant cell gum.

37. The ceramic glaze of claim 23 which comprises from about 0.05% to 3% (w/v) of said cultured plant cell gum.

38. An industrial, pharmaceutical or cosmetic product produced by the method of claim 1.

39. A gel produced by the method of claim 1 wherein said cultured plant cell gum used as said gelling agent is a Phleum plant cell gum.

40. In an industrial, pharmaceutical or cosmetic manufacturing process in which a plant exudate or plant extract gum is employed as a thickening, emulsifying, suspending, waterproofing, gelling, protective collid, stabilizing or coating agent, the improvement wherein said plant exudate or extract gum is replaced with a cultured plant cell gum of a vascular plant product by suspension culture of cells of a plant selected from the group consisting of Nicotiana, Pyrus, Phleum, Lolium, Hibiscus, Lycopersicon, Panicum, Mesembryanthemum, Actindia, Sida, Medicago, Trifolium, Solanum, and Cichorium.

41. The process of claim 40 which guar gum is used as a viscosifying agent, the improvement wherein a cultured plant cell gum of a *Phleum pretense* plant is substituted for guar gum.

42. The process of claim 40 wherein gum arabic is used as an emulsifying agent, the improvement wherein a cultured plant cell gum of a *Nicotiana plumbaginifolia* or a *Pyrus communis* plant is substituted for said gum arabic.

43. The process of claim 40 wherein said cultured plant cell gum is employed in a concentration ranging from about 0.01% to 10% (w/v) dependent upon the application.

44. An isolated plant cell gum produced in suspension cell culture of cells of *Mesembryanthemum chilense* which comprises xyloglucan.

45. An isolated plant cell gum of claim 44 further comprising rhamnogalacturonan.

46. The isolated plant cell gum of claim 44 further comprising AGP.

47. The isolated plant cell gum of claim 44 wherein xyloglucan comprises about 27% by weight of said gum and 3,6-arabinogalactan represents about 18% by weight of said gum.

48. A process for manufacturing an industrial, pharmaceutical or cosmetic product which process comprises a step of including an emulsifying agent in the manufactured product, wherein the emulsifying agent is the plant cell gum of claim 44.

49. A process for manufacturing an industrial, or pharmaceutical product, said process excluding food manufacturing, which process comprises a step of including a viscosifying agent, thickening agent, gelling agent, emulsifying agent, suspending agent, stabilizing agent, encapsulating agent, flocculating agent, film-forming agent, sizing agent, adhesive agent, binding or coating agent, lubricating agent, water retention agent or coagulaltion agent or any combinations of such agents in the manufactured product, wherein a cultured plant cell gum of a vascular plant produced by suspension culture of a plant selected from the group consisting of Nicotiana, Pyrus, Phleum, Lolium, Hibiscus, Lycopersicon, Panicum, Mesembryanthemum, Actindia, Sida, Medicago, Trifolium, Solanum, Cichorium, and Polianthes is used as said agent.

50. The process of claim 49 wherein said vascular plant is *Polianthes tuberosa*.

51. An improved method of making a cultured Pyrus or Nicotiana plant cell gum comprising the steps of:

culturing a Pyrus or Nicotiana plant cell on a medium containing Brewers Liquid Maltose (BLM) as a carbon source in a concentration of between about 80 and 200 g (wet weight) per liter of medium to produce a gum; and recovering said gum.

52. The method of making a cultured plant gum of claim 51 wherein said gum has an enhanced film forming property over gum produced in plant cells grown on sucrose as a carbon source.

53. An improved industrial, pharmaceutical or cosmetic manufacturing process, said process excluding food manufacturing, wherein the improvement comprises using a cultured plant cell gum produced by the method of claim 51.

54. The improved process of claim 53 wherein said cultured plant cell gum is employed as a film-forming agent.

* * * * *

UNITED STATES PATENT AND TRADEMARK OFFICE
CERTIFICATE OF CORRECTION

PATENT NO. : 5,747,297

DATED : May 5, 1998

INVENTOR(S) : Clarke et al.

It is certified that error appears in the above-identified patent and that said Letters Patent is hereby corrected as shown below:

column 3, line 57, delete "40" and substitute --4--.

Column 5, line 23, delete "$Na_2.EDTA$" and substitute --$Na_2EDTA$--.

Column 6, line 43, delete "Phleum pratense" and substitute --*Phleum pratense*--.

Column 10, line 4, insert --,-- after "iron".

Column 10, line 62, insert --,-- after "spraying".

Column 12, line 59, delete "Phleum pratense" and substitute --*Phleum pratense*--.

Column 13, in the list following line 40, delete "$CaCl_2.2H_2O$" and substitute --$CaCl_2 \cdot 2H_2O$--; in the list following line 40, delete "$MgSO_4.7H_2O$" and substitute --$MgSO_4 \cdot 7H_2O$--; in the list following line 60, delete "$MnSO_4.4H_2O$" and substitute --$MnSO_4 \cdot 4H_2O$--; in the list following line 60, delete "$ZnSO_4.7H_2O$" and substitute --$ZnSO_4 \cdot 7H_2O$--; in the list following line 60, delete "$CuSO_4.5H_2O$" and substitute --$CuSO_4 \cdot 5H_2O$--; in the list following line 60, delete "$NaMoO_4.2H_2O$" and substitute --$NaMoO_4 \cdot 2H_2O$--.

Column 14, line 3, delete "$CoCl_2.6H_2O$" and substitute --$CoCl_2 \cdot 6H_2O$--; in the list following line 8, delete "$Na_2EDTA.2H_2O$" and substitute --$Na_2EDTA \cdot 2H_2O$--; in the list following line 8, delete "$FeSo_4.7H_2O$" and substitute --$FeSO_4 \cdot 7H_2O$--; line 16, delete "$FeSO_4.7H_2O$" and substitute --$FeSO_4 \cdot 7H_2O$--; in the list following line 60, delete "$MgSO_4.7H_2O$" and substitute --$MgSO_4 \cdot 7H_2O$--.

UNITED STATES PATENT AND TRADEMARK OFFICE
CERTIFICATE OF CORRECTION

PATENT NO. : 5,747,297

DATED : May 5, 1998

INVENTOR(S) : Clarke et al.

It is certified that error appears in the above-identified patent and that said Letters Patent is hereby corrected as shown below:

Column 15, in the list following line 2, delete "ZnSO4.7H$_2$O" and substitute --ZnSO$_4$·7H$_2$O--; in the list following line 2, delete "MnSO$_4$.H$_2$O" and substitute --MnSO$_4$·H$_2$O--; in the list following line 2, delete "NaMoO$_4$.2H$_2$O" and substitute --NaMoO$_4$·2H$_2$O--; in the list following line 2, delete "CuSO$_4$.5H$_2$O" and substitute --CuSO$_4$·5H$_2$O--; in the list following line 2, delete "CoCl$_2$.6H$_2$O" and substitute --CoCl$_2$·6H$_2$O--; line 29, delete "KH$_2$PO$_1$" and substitute --KH$_2$PO$_4$--; line 34, delete "CaCl$_2$.2H$_2$O" and substitute --CaCl$_2$·2H$_2$O--; in the list following line 35, delete "CaCl$_2$.2H$_2$O" and substitute --CaCl$_2$·2H$_2$O-; line 40, delete "Fe.EDTA" and substitute --Fe·EDTA--; in the list following line 40, delete "FeSO$_4$.7H$_2$O" and substitute --FeSO$_4$·7H$_2$O--; in the list following line 40, delete "Na$_2$EDTA.2H$_2$O" and substitute --Na$_2$EDTA·2H$_2$O--.
Column 16, line 22, delete "cultured" and substitute --cultures--; line 53, delete "800" and substitute --80--.
Column 17, line 6, delete "2-4vol-" and substitute --2-4 vol- --.
Column 19, in the list following line 36, delete "40.00" and substitute --50.00-- in the last entry in the Total row.
Column 20, line 19, delete "1.o" and substitute --1.0--; line 62, delete "60" and substitute --6--.
Column 23, line 1, add a line break after "5. Water".
Column 27, line 29, delete "11.B" and substitute --12.B--.
Column 28, line 37, delete the last "," and substitute --.--; line 43, delete "6-0-Me" and substitute --6-O-Me--.

UNITED STATES PATENT AND TRADEMARK OFFICE
CERTIFICATE OF CORRECTION

PATENT NO. : 5,747,297

DATED : May 5, 1998

INVENTOR(S) : Clarke et al.

It is certified that error appears in the above-identified patent and that said Letters Patent is hereby corrected as shown below:

Column 30, line 24, delete "Fe.EDTA" and substitute --Fe-EDTA--; line 33, delete "Ph" and substitute --pH--.
Table 3, in the column under Caryophyllidea, delete "Alzoacea" and substitute --Aizoacea--; in the column under Mesembrya-, delete "nthemem" and substitute --*nthemem*--; in the first column, delete "*Rhamnogalacturonan Galacturonan*" and substitute --Rhamnogalacturonan Galacturonan--.
In Claim 45, line 40, delete "An" and substitute --The--.
In Claim 49, line 60, delete "coagulaltion" and substitute --coagulation--.
Please delete Table 5 and replace with the following:

Signed and Sealed this

Seventeenth Day of November, 1998

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,747,297

DATED : May 5, 1998

INVENTOR(S) : Clarke et al.

It is certified that error appears in the above-identified patent and that said Letters Patent is hereby corrected as shown below:

Table 5: Plant cell suspension cultures: Explant Source and Culturing Conditions

| Species | Explant | Medium[1] | No. sub-cultures (callus)[2] | No. sub-cultures (suspension) | Age of culture at harvest (days) |
|---|---|---|---|---|---|
| Dicots Caryophyllidae Aizoaceae | | | | | |
| *Mesembryanthemum chilense* | leaf | MS2 | 25 | 6 | 13 |
| Dilleniidae Actinidiaceae | | | | | |
| *Actinidia deliciosa* | fruit with seed | MS9 | 10+ | 4 | 21 |
| Malvaceae | | | | | |
| *Hibiscus esulentus* | seedling stem | MS9 | 7 | 4 | 13 |
| *Sida rhomifolia* | seedling stem | MS9 | 20 | 4 | 14 |

UNITED STATES PATENT AND TRADEMARK OFFICE
CERTIFICATE OF CORRECTION

PATENT NO. : 5,747,297

DATED : May 5, 1998

INVENTOR(S) : Clarke et al.

It is certified that error appears in the above-identified patent and that said Letters Patent is hereby corrected as shown below:

Table 5 continued

| | | | | | |
|---|---|---|---|---|---|
| Rosidae<br>Rosaceae | | | | | |
| *Pyrus communis*[3] | fruit | pear BAL | 24 | 7 | 11 |
| Fabaceae | | | | | |
| *Medicago sativa* | seed | MS1 + NOA | 20+ | 3 | 6 |
| *Trifolium repens* | seed | MS9 | 10+ | 3 | 14 |
| *Trifolium pratense* | seed | MS6 | 0 | 3 | 11 |
| Asteridae<br>Solanaceae | | | | | |
| *Solanum tuberosum* | growing points | MS6 | 18 | 5 | 18 |
| *Lycopersicon esculentum* | fruit | tomato BAL | 20+ | 2 | 12 |
| Asteraceae | | | | | |
| *Cichorium intybus* | DSM-Gmbh[4] | LS | 11+ | 7 | 11 |

UNITED STATES PATENT AND TRADEMARK OFFICE
CERTIFICATE OF CORRECTION

PATENT NO.   :   5,747,297

DATED        :   May 5, 1998

INVENTOR(S)  :   Clarke et al.

It is certified that error appears in the above-identified patent and that said Letters Patent is hereby corrected as shown below:

Table 5 continued

| Monocots | | | | | |
|---|---|---|---|---|---|
| Commelinidae Poaceae | | | | | |
| *Phleum pratense* | seed | MS + 2,4-D$^5$ | 0 | 3 | 14 |
| *Panicum miliaceum* | seed | MS3/MS9 | 2 | 4 | 14 |
| Lilidae Agavaceae | | | | | |
| *Polianthes tuberosa* | leaf | MS17 | 10 | 3 | 18 |

MS1 = MS powder with 0.5 mg/L 2,4-D (2,4-dichlorophenoxyacetic acid);
MS2 = MS powder with 2.0 mg/L 2,4-D;
MS3 = MS powder with 4.0 mg/L 2,4-D;
MS6 = MS powder with 4.0 mg/L 2,4-D and 1.075 mg/L mixed cytokinins;
MS9 = MS powder with 4.0 mg/L 2,4-D and 2.150 mg/L mixed cytokinins;
MS17 = MS powder with 2.0 mg/L NAA (1-naphthaleneacetic acid) and 2.0 mg/L BAP (6-benzylaminopurine);
LS = LS powder with 0.2 mg/L 2,4-D and 0.04 mg/l NAA, see text Example 14;
tomato BAL, see text Example 14;
NOA = napthoxyacetic acid used at final concentration 0.5 mg/L;
Concentration of 2,4-D in *Phleum pratense* culture is 2.0 mg/L
"+" means more, i.e., 10+ means more than 10.
Brown pear.
Commercial source of plant cell culture; Deutsche Sammlung von Mikroorganismen und Zelkulturen.
Millet has been grown on both MS3 and MS9 with substantially the same results. The specific results shown were obtained on MS9.